(12) United States Patent
Kaczmarczyk et al.

(10) Patent No.: US 10,538,743 B2
(45) Date of Patent: *Jan. 21, 2020

(54) DELIVERY OF PACKAGED RNA TO MAMMALIAN CELLS

(71) Applicant: The USA, as represented by the Secretary, Dept. of Health and Human Services, Bethesda, MD (US)

(72) Inventors: Stanislaw J. Kaczmarczyk, Frederick, MD (US); Deb K. Chatterjee, Potomac, MD (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/190,992

(22) Filed: Jun. 23, 2016

(65) Prior Publication Data

US 2016/0340653 A1 Nov. 24, 2016

Related U.S. Application Data

(63) Continuation of application No. 14/388,441, filed as application No. PCT/US2013/031876 on Mar. 15, 2013, now abandoned.

(60) Provisional application No. 61/615,687, filed on Mar. 26, 2012.

(51) Int. Cl.
| | | |
|---|---|---|
| C12N 15/86 | (2006.01) | |
| C12N 7/00 | (2006.01) | |
| A61K 35/76 | (2015.01) | |
| A61K 38/17 | (2006.01) | |
| A61K 48/00 | (2006.01) | |
| C12N 15/113 | (2010.01) | |

(52) U.S. Cl.
CPC .............. *C12N 7/00* (2013.01); *A61K 35/76* (2013.01); *A61K 38/1774* (2013.01); *A61K 48/0066* (2013.01); *C12N 15/113* (2013.01); *C12N 15/86* (2013.01); *C12N 2310/11* (2013.01); *C12N 2310/141* (2013.01); *C12N 2320/32* (2013.01); *C12N 2740/11022* (2013.01); *C12N 2740/11023* (2013.01); *C12N 2740/11042* (2013.01); *C12N 2740/11051* (2013.01); *C12N 2740/13022* (2013.01); *C12N 2740/13051* (2013.01); *C12N 2770/36123* (2013.01); *C12N 2770/36143* (2013.01); *C12N 2770/36145* (2013.01); *C12N 2770/36152* (2013.01); *C12N 2800/24* (2013.01); *C12N 2810/6081* (2013.01)

(58) Field of Classification Search
None
See application file for complete search history.

(56) References Cited

U.S. PATENT DOCUMENTS

| | | |
|---|---|---|
| 5,071,651 A | 12/1991 | Sabara et al. |
| 5,374,426 A | 12/1994 | Sabara et al. |
| 5,631,237 A | 5/1997 | Dzau et al. |
| 6,099,847 A | 8/2000 | Tobin et al. |
| 6,541,010 B1 | 4/2003 | Johnston et al. |
| 6,783,939 B2 | 8/2004 | Olmsted et al. |
| 6,902,886 B1 | 6/2005 | Citovsky et al. |
| 7,425,337 B2 | 9/2008 | Smith et al. |
| 9,296,790 B2 | 3/2016 | Chatterjee et al. |
| 1,004,083 A1 | 8/2018 | Chatterjee et al. |
| 2002/0052040 A1 | 5/2002 | Hunt |
| 2002/0177551 A1 | 11/2002 | Terman |
| 2008/0118956 A1 | 5/2008 | Pages et al. |
| 2011/0250675 A1 | 10/2011 | Bennet et al. |
| 2015/0050243 A1 | 2/2015 | Kaczmarczyk et al. |
| 2016/0312242 A1 | 10/2016 | Chatterjee et al. |

FOREIGN PATENT DOCUMENTS

| | | |
|---|---|---|
| JP | 2007-512827 | 5/2007 |
| WO | WO 92/11291 | 7/1992 |
| WO | WO 96/30523 | 10/1996 |
| WO | WO 98/15631 | 4/1998 |
| WO | WO 01/44481 | 6/2001 |
| WO | WO 03/024481 | 3/2003 |
| WO | WO 2005/042695 | 5/2005 |
| WO | WO 2005/115444 | 12/2005 |
| WO | WO 2006/059141 | 6/2006 |
| WO | WO 2007/130330 | 11/2007 |
| WO | WO 2008/115199 | 9/2008 |
| WO | WO 2011/056899 | 5/2011 |
| WO | WO 2013/148302 | 10/2013 |

OTHER PUBLICATIONS

Weldon et al Incorporation of Chimeric Gag Protein into Retroviral Particles Journal of Virology, Sep. 1990, p. 4169-4179.*
Freed et al 1998 MINIREVIEW HIV-1 Gag Proteins: Diverse Functions in the Virus Life Cycle; pp. 1-15.*
CD80 From Wikipedia, the free encyclopedia pp. 1-6; dowloaded on Dec. 5, 2018.*
Siegel et al., Sequence-specific recognition of a subgenomic RNA promoter by a viral RNA polymerase Proc. Natl. Acad. Sci. USA vol. 94, pp. 11238-11243, Oct. 1997.*

(Continued)

*Primary Examiner* — Maria G Leavitt
(74) *Attorney, Agent, or Firm* — Sheridan Ross P.C.

(57) ABSTRACT

Described herein are compositions relating to alphavirus-based virus-like particles (VLPs) and methods for making and using the described VLPs. The described compositions include VLPs and vectors and cells used to produce the VLPs. Also included are related methods to produce the VLPs, to transduce cells using the VLPs, and to produce a protein or polynucleotide of interest in a target cell using the VLPs. Also described are alphavirus-based replicons that allow for expression of proteins or polynucleotides of interest in a target cell without a cytopathic effect.

7 Claims, 12 Drawing Sheets

Figure 1A:
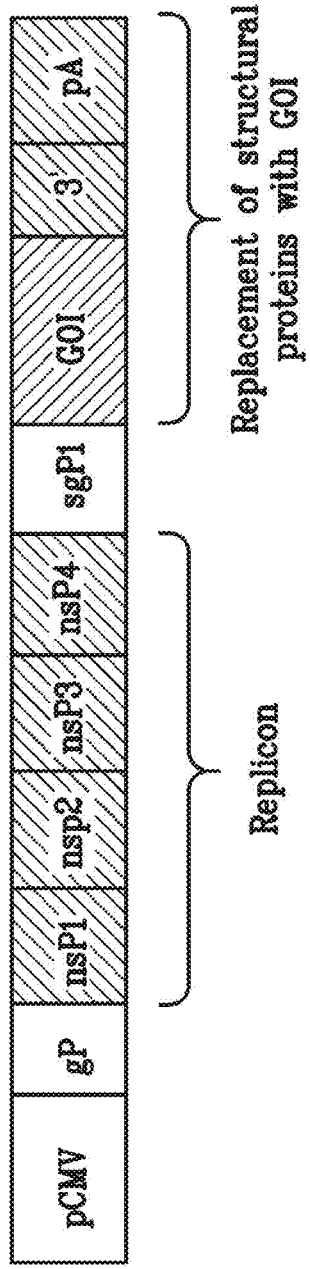

Specification includes a Sequence Listing.

(56) References Cited

OTHER PUBLICATIONS

Armstrong et al. "Major histocompatibility complex calss II-transsfected tumor cells present endogenous antigen and are potent inducers of tumor-specific immunity," Proceedings of the National Academy of Sciences, Jun. 1997, vol. 94, No. 13, pp. 6886-6891.
Lin et al. "Treatment of Established Tumors with a Novel Vaccine That Enhances Major Histocompatibility Class II Presentation of Tumor Antigen," Cancer Research, Jan. 1996, vol. 56, No. 1, pp. 21-26.
Pulaski et al. "Immunotherapy with vaccines combining MHC class II/CD80+ tumor cells with interleukin-12 reduces established metastatic disease and stimulates immune effectors and monokine induced by interferon y," Cancer Immunology and Immunotherapy, Jan. 2000, vol. 49, No. 1, pp. 34-45.
Pulaski et al. "Reduction of Established Spontaneous Mammary Carcinoma Metastases following Immunotherapy with Major Histocompatibility Complex Class II and B7.1 Cell-based Tumor Vaccines," Canser Research, Jan. 1998, vol. 58, No. 7, pp. 1486-1493.
Pulaski et al. "Cooperativity of *Staphylococcal aureus* Enterotoxin B Superantigen, Major Histocompatibility Complex Class II, and CD80 for Immunotherapy of Advanced Spontaneous Metastases in a Clinically Relevant Postoperative Mouse Breast Cancer model," Cancer Research, May 2000, vol. 60, No. 10, pp. 2710-2715.
Reiser et al. "Induction of B7-1 in podocytes is associated with nephrotic syndrome," Journal of Clinical Investigation, May 2004, vol. 113, No. 10, pp. 1390-1397.
Official Action for European Patent Application No. 13712661.1, dated Mar. 9, 2017 8 pages.
English Translation of Official Action for Japan Patent Application No. 2015-503322, dated Jan. 24, 2017 3 pages.
Akkina et al., "High-efficiency gene transfer into CD34+ cells with a human immunodeficiency virus type 1-based retroviral vector pseudotyped with vesicular stomatitis virus envelope glycoprotein G.", J Virol. 1996, vol. 70(4), pp. 2581-2585.
Alefantis et al., "Characterization of a Nuclear Export Signal within the Human T Cell Leukemia Virus Type I Transactivator Protein Tax," The Journal of Biological Chemistry, 2003, vol. 278(24), pp. 21814-21822.
Altschul et al., "Basic Local Alignment Search Tool," Journal of Molecular Biology, 1990, vol. 215, pp. 403-410.
Altschul et al., "Gapped BLAST and PSI-BLAST: a new generation of protein database search programs," Nucleic Acids Research, 1997, vol. 25(17), pp. 3389-3402.
Anderson "Tumor Vaccines for Breast Cancer," Cancer Invest., May 2009, vol. 27, No. 4, pp. 361-368.
Bogerd et al., Protein Sequence Requirements for Function of the Human T-Cell Leukemia Virus Type 1 Rex Nuclear Export Signal Delineated by a Novel in Vivo Randomization-Selection Assay, Molecular and Cellular Biology, 1996, vol. 16(8), pp. 4207-4214.
Briggs, "The stoichiometry of Gag protein in HIV-1," Nature Structural & Molecular Biology, 2004, vol. 11(7), pp. 672-675.
Carriere et al., "Sequence Requirements for Encapsidation of Deletion Mutants and Chimeras of Human Immunodeficiency Virus Type 1 Gag Precursor into Retrovirus-Like Particles," Journal of Virology, 1995, vol. 69(4), pp. 2366-2377.
Chauhan et al., "The taming of the cell penetrating domain of the HIV Tat: Myths and realities," Journal of Controlled Release, 2007, vol. 117, pp. 148-162.
Chazal et al., "Virus Entry, Assembly, Budding, and Membrane Rafts," Microbiology and Molecular Biology Reviews, 2003, vol. 67(2), pp. 226-237.
Coskun-Ari et al., "Sequence-specific Interactions in the Tus-Ter Complex and the Effect of Base Pair Substitutions on Arrest of DNA Replication in *Escherichia coli*," The Journal of Biological Chemistry, 1997, vol. 272(42), pp. 26448-26456.

Cyert, "Regulation of Nuclear Localization during Signaling," The Journal of Biological Chemistry, 2001, vol. 276(24), pp. 20805-20808.
Deml et al. "Recombinant HIV-1 Pr55gag virus-like particles: potent stimulators of innate and acquired immune responses," Molecular Immunology, 2005, vol. 42(2), pp. 259-277.
Deo et al. "Expression of an RSV-gag virus-like particle in insect cell lines and silkworm larvae," Journal of Virological Methods, 2011, vol. 177, pp. 147-152.
Dunn et al. "Retroviral proteases," Genome Biology, 2002, vol. 3(4), pp. 3006.1-3006.7.
Dworetzky et al., "Translocation of RNA-Coated Gold Particles Through the Nuclear Pores of Oocytes," The Journal of Cell Biology, 1988, vol. 106, pp. 575-584.
Facke et al., "A Large Deletion in the Matrix Domain of the Human Immunodeficiency Virus gag Gene Redirects Virus Particle Assembly from the Plasma Membrane to the Endoplasmic Reticulum," Journal of Virology, 1993, vol. 67(8), pp. 4972-4980.
Fischer et al., "The HIV-1 Rev Activation Domain Is a Nuclear Export Signal That Accesses an Export Pathway Used by Specific Cellular RNAs," Cell, 1995, vol. 82, pp. 475-483.
Fornerod et al., "CRM1 Is an Export Receptor for Leucine-Rich Nuclear Export Signals," Cell, 1997, vol. 90, pp. 1051-1060.
Gangeten et al., "Brief expression of a GFPcre fusion gene in embryonic stem cells allows rapid retrieval of site-specific genomic deletions," Nucleic Acids Research, 1997, vol. 25(16), pp. 3326-3331.
Gerace, "Nuclear Export Signals and the Fast Track to the Cytoplasm," Cell, 1995, vol. 82, pp. 341-344.
Gonzalez-Navajas et al. "Immunomodulatory functions of type 1 interferons," Nature Review Immunology, col. 12, 2012, pp. 125-135.
Gorlich et al., "Nucleocytoplasmic Transport," Science, 1996, vol. 271, pp. 1513-1518.
Gottlieb et al., "Equilibrium, Kinetic, and Footprinting Studiesof the Tus-Ter Protein-DNA Interaction," The Journal of Biological Chemistry, 1992, vol. 267(11), pp. 7434-7443.
Gottlinger et al., "Role of capsid precursor processing and myristoylation in morphogenesis and infectiveity of human immunodeficiency virus type 1," PNAS, 1989, vol. 86(15), pp. 5781-5785.
Guibinga et al. "Baculovirus GP64-Pseudotyped HIV-Based Lentivirus Vectors are Stabilized Against Complement Inactivation by Codisplay of Decay Accelerating Factor (DAF) or of a GP64-DAF Fusion Protein," Molecular Therapy, 2005, vol. 11(4), pp. 645-651.
Haglund et al. "Expression of Human Immunodeficiency Virus Type 1 Gag Protein Precursor and Envelope Proteins from a Vesicular Stomatitis Virus Recombinant: High-Level Production of Virus-like Particles Containing HIV Envelope," Virology, 2000, vol. 268, pp. 112-121.
Hajek et al. "Proteolytic Processing and Assembly of gag and gag-pol Proteins of TED, a Baculovirus-Associated Retrotransposon of the Gypsy Family," Journal of Virology, 1998, vol. 72(11), pp. 8718-8724.
Harvey et al. Tetracycline-Inducible Packaging Cell Line for Production of Flavivirus Replicon Particles, Journal of Virology, 2004, vol. 78(1), pp. 531-538.
Hong et al., "Assembly-Defective Point Mutants of the Human Immunodeficiency Virus Type 1 Gag Precursor Phenotypically Expressed in Recombinant Baculovirus-Infected Cells," Journal of Virology, 1993, vol. 67(5), pp. 2787-2798.
Ikuta et al., "Nuclear Localization and Export Signals of the Human Aryl Hydrocarbon Receptor," The Journal of Biological Chemistry, 1998, vol. 273(5), pp. 2895-2904.
Jans et al., "Nuclear targeting signal recognition: a key control point in nuclear transport?," BioEssays 22.6, pp. 532-544.
Jiang et al., "Norwalk Virus Genome Cloning and Characterization," Science, 1990, vol. 250, pp. 1580-1583.
Kalderon et al., "A Short Amino Acid Sequence Able to Specify Nuclear Location," Cell, 1984, vol. 39, pp. 499-509.
Kamada et al., "Structure of a replication-terminator protein complexed with DNA," Nature, 1996, vol. 383, pp. 598-603.

(56) References Cited

OTHER PUBLICATIONS

Karliin et al., "Methods for assessing the statistical significance of molecular sequence features by using general scoring schemes," PNAS, 1990, vol. 87, pp. 2264-2268.
Karlin et al., "Applications and statistics for multiple high-scoring segments in molecular sequences," PNAS, 1993, vol. 90, pp. 5873-5877.
Kent et al. "Evaluation of recombinant Kunjin replicon SIV vaccines for protective efficacy in macaques," Virology, 2008, vol. 374(2), pp. 528-534.
Kuempel et al., "Bidirectional Termination of Chromosome Replication in *Escherichia coli*," Moled. Gen. Genet., 1973, vol. 125, pp. 1-8.
Kurisaki et al., "The Mechanism of Nuclear Export of Smad3 Involves Exportin 4 and Ran," Molecular and Cellular Biology, 2006, Voo. 26(4), pp. 1318-1332.
Le et al., "Nuclear targeting determinants of the phage P1 Cre DNA recombinase," Nucleic Acids Research, 1999, vol. 27(24), pp. 4703-4709.
Lewis et al. "Development of an Avian Leukosis-Sarcoma Virus Subgroup A Pseudotyped Lentiviral Vector," Journal of Virology, 2001, vol. 75(19), pp. 9339-9344.
Link et al., "Therapeutic protein transduction of mammalian cells and mice by nucleic acid-free lentiviral nanoparticles," Nucleic Acids Research, 2006, vol. 34(2), e16, pp. 1-10.
Luo et al. "Chimeric gag-V3 virus-like particles of human immunodeficiency virus induce virus-neutralizing antibodies," PNAS, Nov.1992, vol. 89, No. 21, pp. 10527-10531.
Luo et al. "Induction of V3-Specific Cytotoxic T Lymphocyte Responses by HIV gag Particles Carrying Multiple Immunodominant V3 Epitopes of gp 120," Virology, 1998, vol. 240, pp. 316-325.
Masters et al., "Evidence for the Bidirectional Replication of the *Escherichia coli* Chromosome," Nature New Bioology, 1971, vol. 232, pp. 137-140.
Matsui et al., "The Isolation and Characterization of a Norwalk Virus-specific cDNA," Journal of Clinical Investigation, 1991, vol. 87, pp. 1456-1461.
Mazarakis et al. "Rabies virus glycoprotein pseudotyping of lentiviral vectors enables retrograde axonal transport and access to the nervous system after peripheral delivery," Human Molecular Genetics, 2001, vol. 10(19), pp. 2109-2121.
Mervis et al. "The gag gene products of human immunodeficiency virus type 1: alignment within the gag open reading frame, identification of posttranslational modifications, and evidence for alternative gag precursors." Journal of Virology, 1988, vol. 62(11 ), pp. 3993-4002.
Michel et al. "Optimisation of secretion of recombinant HBsAg virus-like particles: Impact on the development of HIV-1/HBV bivalent vaccines," Vaccine, 2007, 2006, vol. 25, pp. 1901-1911.
Moll et al., "Designed heterodimerizing leucine zippers with a range of pIs and stabilities up to 10-15 M," Protein Science, 2001, vol. 10, pp. 649-655.
Morling et al. "Masking of Retroviral Envelope Functions by Oligomerizing Polypeptide Adaptors," Virology, 1997, vol. 234, pp. 51-61.
Mulugu et al., "Mechanism of termination of DNA replication of *Escherichia coli* involves helicase-contrahelicase interaction," PNAS, 2001, vol. 98(17), pp. 9569-9574.
Murriel et al., "Influence of protein transduction domains on intracellular delivery of macromolecules," Expert Opinion on Drug Delivery, 2006, vol. 3(6), pp. 739-746.
Naldini et al. "Efficient transfer, integration, and sustained long-term expression of the transgene in adult rat brains injected with a lentiviral vector," PNAS, 1996, vol. 93, pp. 11382-11388.
Naldini et al. "In Vivo Gene Delivery and Stable Transduction of Nondividing Cells by a Lentiviral Vector," Science, 1996, vol. 272, pp. 263-267.
Newmeyer et al., "Nuclear Import Can Be Separated into Distinct Steps in Vitro: Nuclear Pore Binding and Translocation," Cell, 1988, vol. 52, pp. 641-653.
Neylon et al., "Interaction of the *Escherichia coli* Replication Terminator Protein (Tus) with DNA: A Model Derived from DNA-Binding Studies of Mutant Proteins by Surface Plasmon Resonance," Biochemistry, 2000, vol. 39, pp. 11989-11999.
Neylon et al., Replication Termination in *Escherichia coli*: Structure and Antihelicase Activity of the Tus-Ter Complex, Microbiology and Molecular Biology Reviews, 2005, vol. 69(3), pp. 501-526.
Owais et al., "Liposome-mediated cytosolic delivery of macromolecules and its possible use in vaccine development," European Journal of Biochemistry, 2000, vol. 267, pp. 3946-3956.
Patel et al., "Natively Unfolded Nucleoporins Gate Protein Diffusion across the Nuclear Pore Complex," Cell, 2007, vol. 129, pp. 83-96.
Peitz et al., "Ability of the hydrophobic FGF and basic TAT peptides to promote cellular uptake of recombinant Cre recombinase: A tool for efficient genetic engineering of mammalian genomes," PNAS, 2002, vol. 99(7), pp. 4489-4494.
Pelczar et al., "Agrobacterium proteins VirD2 and VirE2 mediate precise integration of synthetic T-DNA complexes in mammalian cells," European Molecular Biology Organization, 2004, vol. 5(6), pp. 632-637.
Peretti et al: "Cell Death Induced by the Herpes Simplex Virus-1 Thymidine Kinase Delivered by Human Immunodeficiency Virus-1-Based Virus-like Particles", Molecular Therapy7, Acaemic Press, 2005, vol. 12(6), pp. 1185-1196.
Perez et al. "The Transmembrane Glycoprotein of Human Immunodeficiency Virus Type 1 Induces Syncytium Formation in the Absence of the Receptor Binding Glycoprotein," Journal of Virology, 1992, vol. 66(7), pp. 4134-4143.
Richardson et al., "Nuclear Protein Migration Involves Two Steps: Rapid Binding at the Nuclear Envelope Followed by Slower Translocation through Nuclear Pores," Cell, 1988, vol. 52, pp. 655-664.
Robbins et al., "Two Interdependent Basic Domains in Nucleoplasmin Nuclear Targeting Sequence: Identification of a Class of Bipartite Nuclear Targeting Sequence," Cell, 1991, vol. 64, pp. 615-623.
Royer et al., "Expression and Extracellular Release of Human Immunodeficiency Virus Type 1 Gag Precursors by Recombinant Baculovirus-Infected Cells," Journal of Virology, 1992, vol. 66(5), pp. 3230-3235.
Sasnauskas et al., "Generation of Recombinant Virus-Like Particles of Human and Non-Human Polyomaviruses in Yeast *Saccharomyces cerevisiae*," Intervirology, 2002, vol. 45, pp. 308-317.
Sasnauskas et al., "Yeast Cells Allow High-Level Expression and Formation of Polyomavirus-Like Particles," Biological Chemistry, 1999, vol. 380, pp. 381-386.
Schwarze et al., "Protein transduction: unrestricted delivery into all cells?," Cell Biology, 2000, vol. 10, pp. 290-295.
Skokotas et al., "Mutations in the *Escherichia coli* Tus Protein Define a Domain Positioned Close to the DNA in the Tus-Ter Complex," The Journal of Biological Chemistry, 1995, vol. 270(52), pp. 30941-30948.
Smit et al. "Flavivirus Cell Entry and Membrane Fusion," Virus, 2011, vol. 3, pp. 160-171.
Spearman et al., "Identification of Human Immunodeficiency Virus Type 1 Gag Protein Domains Essential to Membrane Binding and Particle Assembly," Journal of Virology, 1994, vol. 68(5), pp. 3232-3242.
Tsuji et al. "Production of Rous sarcoma virus-like particles displaying human transmembrane protein in silkworm larvae and its application to ligand-receptor binding assay," Journal of Biotechnology, 2011, vol. 155, pp. 185-192.
Twomey et al., "Structure and immunogenicity of experimental foot-and-mouth disease and poliomyelitis vaccines," Vaccine, 1995, vol. 13(16), pp. 1603-1610.
Ulrich et al., "Core Particles of Hepatitis B Virus as Carrier for Foreign Epitopes," Advances in Virus Research, 1998, vol. 50, pp. 141-182.
Varnavski et al. "Noncytopathic Flavivirus Replicon RNA-Based System for Expression and Delivery of Heterologous Genes," Virology 1999, vol. 255(2), pp. 366-375.
Wagner et al. "Construction, Expression, and Immunogenicity of Chimeric HIV-1 Virus-like Particles," Virology, 1996, vol. 220, pp. 128-140.

(56) References Cited

OTHER PUBLICATIONS

Warnes et al., "Expression of the measles virus nucleoprotein gene in *Escherichia coli* and assembly of nucleocapsid-like structures," Gene, 1995, vol. 160, pp. 173-178.
Wilk et al., "Organization of Immature Human Immunodeficiency Virus Type 1," Journal of Virology, 2001, vol. 75(2), pp. 759-771.
Official Action for Australia Patent Application No. 2013240248, dated Dec. 11, 2017 3 pages.
Official Action for European Patent Application No. 13712661.1, dated Jan. 31, 2018 5 pages.
Official Action with English Translation for Japan Patent Application No. 2015-503322, dated Dec. 12, 2017 9 pages.
Official Action with English Translation for Japan Patent Application No. 2015-503322, dated Sep. 25, 2018 7 pages.
Summons to Attend Oral Proceedings for European Patent Application No. 13712661.1, dated Mar. 29, 2019 7 pages.
Bredenbeek et al. "Sindbis Virus Expression Vectors: Packaging of RNA Replicons by Using Defective Helper RNAs," Journal of Virology, Nov. 1993, vol. 67, No. 11, pp. 6439-6446.
Diatta et al. "Semliki Forest virus-derived virus-like particles: characterization of their production and transduction pathways," Journal of General Virology, Nov. 2005, vol. 86, pp. 3129-3136.
Frolov et al. "Selection of RNA Replicons Capable of Persistent Noncytopathic Replication in Mammalian Cells," Journal of Virology, May 1999, vol. 73, No. 5, pp. 3854-3865.
Harvey et al. "Kunjin Virus Replicon Vectors for Human Immunodeficiency Virus Vaccine Development," Journal of Virology, Jul. 2003, vol. 77, No. 14, pp. 7796-7803.
Jurgens et al. "A Novel Self-Replicating Chimeric Lentivirus-Like Particle," Journal of Virology, Jan. 2012, vol. 86, No. 1, pp. 246-261.
Kaczmarczyk et al. "Protein delivery using engineered virus-like particles," Proceedings of the National Acadamy of Science USA, Oct. 2011, vol. 108, No. 41, pp. 16998-17003.
Li et al. "Production of infectious recombinant Moloney murine leukemia virus particles in BHK cells using Semliki Forest virus-derived RNA expression vectors," Proceedings of the National Acadamy of Science USA, Oct. 1996, vol. 93, pp. 11658-11663.
Piver et al. "Mobilization of Full-Length Semliki Forest Virus Replicon by Retrovirus Particles," Journal of Virology, Oct. 2006, vol. 80, No. 19, pp. 9889-9895.
Schell et al. "Significant Protection against High-Dose Simian Immunodeficiency Virus Challenge Conferred by a New Prime-Boos Vaccine Regimen," Journal of Virology, Jun. 2011, vol. 85, No. 12, pp. 5764-5772.
Xiong et al. "Sindbis virus: an efficient, broad host range vector for gene expression in animal cells," Science, Mar. 3, 1989, vol. 243, No. 4895, pp. 1188-1191.
International Search Report and Written Opinion for International (PCT) Patent Application No. PCT/US2013/031876, dated Jul. 8, 2013 12 pages.
International Preliminary Report on Patentability for International (PCT) Patent Application No. PCT/US2013/031876, dated Oct. 1, 2014 7 pages.
Official Action for European Patent Application No. 13712661.1, dated May 24, 2016 3 pages.
Official Action for U.S. Appl. No. 14/388,441, dated May 13, 2015 9 pages. Restriction Requirement.
Official Action for U.S. Appl. No. 14/388,441, dated Sep. 4, 2015 14 pages.
Notice of Allowance for U.S. Appl. No. 14/388,441, dated May 11, 2016 10 pages.

\* cited by examiner

FIG. 5B
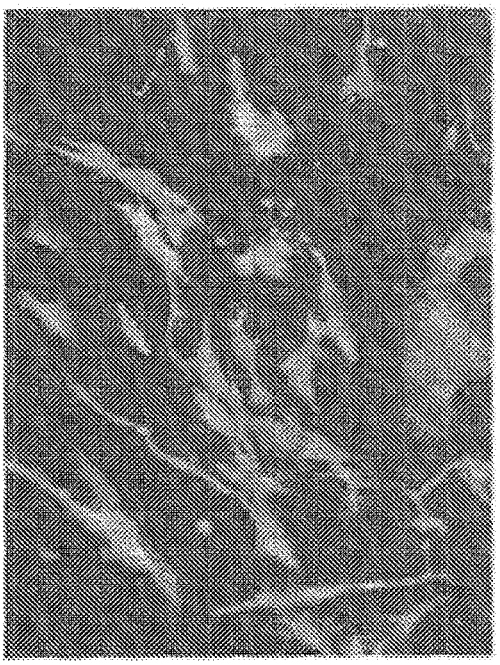
FIG. 5D
FIG. 5C
FIG. 5A

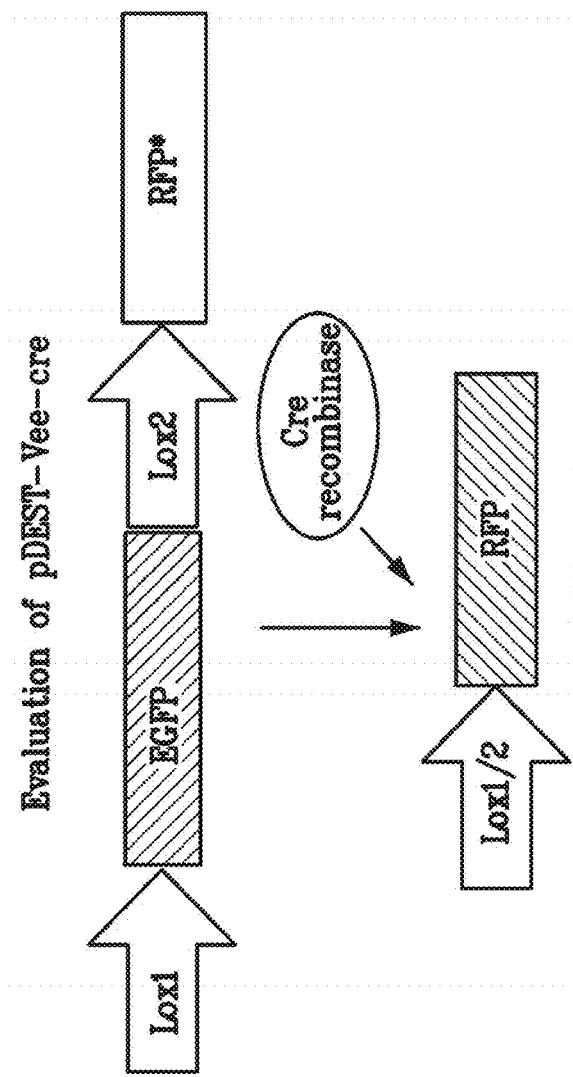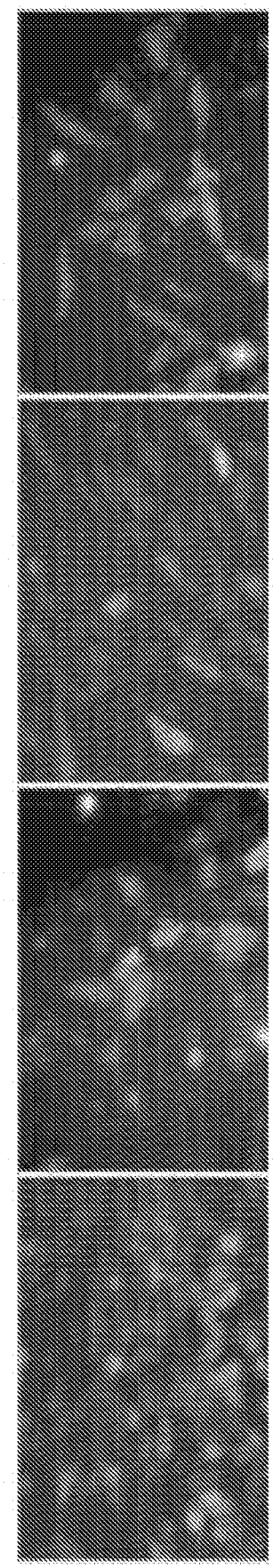
FIG. 7A
FIG. 7B

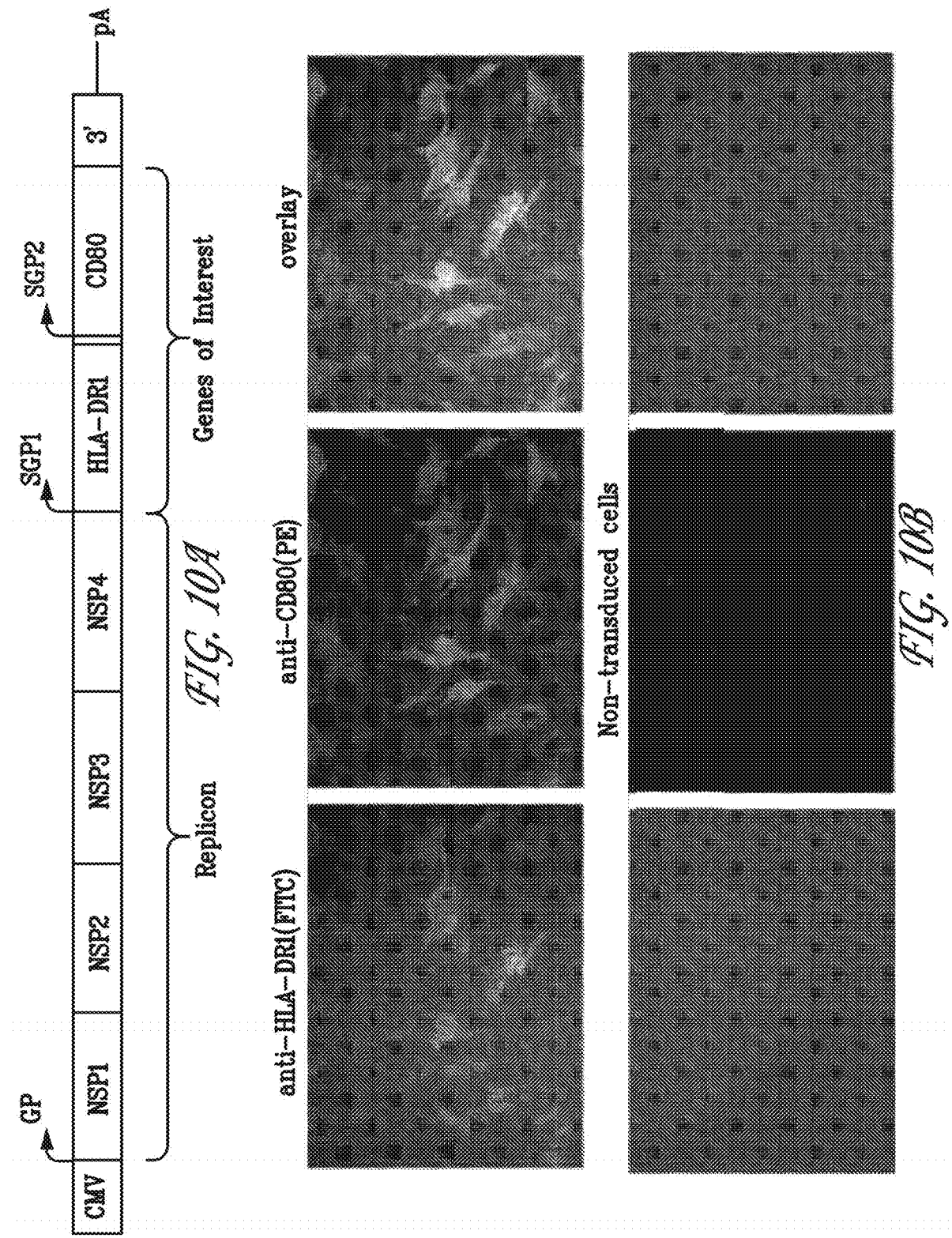

DELIVERY OF PACKAGED RNA TO MAMMALIAN CELLS

CROSS REFERENCE TO RELATED APPLICATIONS

The application is a continuation of U.S. patent application Ser. No. 14/388,441, filed Sep. 26, 2014, now U.S. Pat. No. 9,506, 041, which claims the benefit of application number PCT/US2013/031876, filed Mar. 15, 2013, which claims the benefit of U.S. Provisional Application No. 61/615,687 filed Mar. 26, 2012, which is hereby incorporated by reference in its entirety.

TECHNICAL FIELD

The invention described herein relates to delivering and transcribing recombinant polynucleotides to mammalian cells using replication-defective virus-like particles.

BACKGROUND

Alphaviruses belong to the group IV Togaviridae family of viruses. The alphaviruses are small, spherical, enveloped viruses with a genome of a single positive sense strand RNA. The total genome length ranges between 11,000 and 12,000 nucleotides, and has a 5' cap, and 3' poly-A tail. The four non-structural protein genes (NSP genes) are encoded in the 5' two-thirds of the genome, while the three structural proteins are translated from a subgenomic mRNA colinear with the 3' one-third of the genome.

There are two open reading frames (ORFs) in the alphavirus genome, non-structural and structural. The first includes NSP genes and encodes proteins (nsP1-nsP4) necessary for transcription and replication of viral RNA. The second encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion.

The Sindbis (and VEEV) virus is an alphavirus whose genome comprises a positive mRNA strand of 11703 nucleotides. This virus infects a variety of vertebrate hosts. The genome of Sindbis virus encodes nonstructural (NS, replicon) and structural proteins (capsid and pH dependent fusogenic envelope) that are directly translated in the cytoplasm of the host cell. The alphaviruses also include Aura virus, Babanki virus, Barmah Forest virus, Bebaru virus, Cabassou virus, Chikungunya virus, Eastern equine encephalitis virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus, Salmon pancreas disease virus, Semliki Forest virus, Southern elephant seal virus, Tonate virus, Trocara virus, Una virus, Venezuelan equine encephalitis virus, Western equine encephalitis virus, and Whataroa virus.

Infection of host cell with an alphavirus results in cytotoxicity culminating with apoptosis, This is mostly due to both: expression of alphavirus genomic RNA in large quantities triggering antiviral state in host cells and direct interaction of alphaviral non-structural proteins ( NSP2 of SIN or NC of VEEV) with cellular mRNA synthesis or translational shut-off causing cytophathic effect (CPE) on host cell host cell. A natural Sindbis virus variant containing a point mutation in one of the nonstructural proteins, NSP2 (at position 726) demonstrated sustained and noncytopathic growth in infected cells although the viral titer recovered from infected cells was substantially reduced (Frolov, I. et al., J. Virol. 3845-65 (May, 1999)).

Alphaviruses are of interest to gene therapy researchers. Ross River virus, Sindbis virus, Semliki Forest virus (SFV), and Venezuelan equine encephalitis virus (VEEV) have all been used to develop vectors for gene delivery. Pseudotyped viruses may be formed by combining alphaviral envelopes glycoproteins and retroviral capsids. Alphaviral envelope glycoproteins pseudotyped retroviruses or lentiviruses are able to integrate the genes that they carry into the potential host cells. The pseudotyped alphaviruses are recognized and infected by the alphaviral envelope proteins E2 and E1. Stable integration of viral genes is mediated by retroviral interiors of these vectors.

There are limitations to the use of alphaviruses in the field of gene therapy due to their lack of specificity of targeting. However, through the introduction of variable antibody domains in a non-conserved loop in the structure of E2, specific populations of cells have been targeted. Furthermore, the use of whole alphaviruses for gene therapy is of limited efficacy both because several internal alphaviral proteins are involved in the induction of apoptosis upon infection and also because the alphaviral capsid mediates only the transient introduction of mRNA into host cells. Neither of these limitations extends to alphaviral envelope pseudotypes of retroviruses or lentiviruses.

SUMMARY

One aspect of the description is a virus-like particle (VLP) comprising an alphavirus replicon, wherein the alphavirus replicon comprises a recombinant polynucleotide, a retroviral gag protein, a fusogenic envelope protein, in which the VLP does not contain an alphavirus structural protein gene. The alphavirus replicon may be derived from Sindbis virus or VEEV nonstructural proteins NSP1, NSP2, NSP3, and NSP4, and a retroviral packaging signal. The retroviral gag protein may be derived from Rous sarcoma virus or murine leukemia virus. The fusogenic envelope protein is selected from the group consisting of haemagglutinin, Rous sarcoma virus (RSV) fusion protein, an E protein of tick borne encephalitis virus and dengue fever virus, the E1 protein of SFV, baculovirus gp64, and Vesicular stomatitis (Indiana) virus-G (VSV-G) protein, preferably a glycoprotein, or fragment or derivative thereof, more preferably from a RNA virus or a retrovirus, or fragment or derivative thereof, most preferably VSV-G or EnvA, or an alteration of VSV-G. The VLP described herein may be capable of binding to a eukaryotic cell, preferably a human cell. The binding of the VLP may be specific to a target cell. The VLP described herein preferably replicates in the target cell. In some embodiments the VLP described herein is not cytopathic to the cell. The recombinant polynucleotide of the VLP may comprise a miRNA, shRNA or an antisense RNA, preferably a shRNA or antisense RNA that knocks down expression of a gene in the cell. The recombinant polynucleotide of the VLP may comprise an RNA encoding a protein that can be expressed by the cell.

Figure 6A:
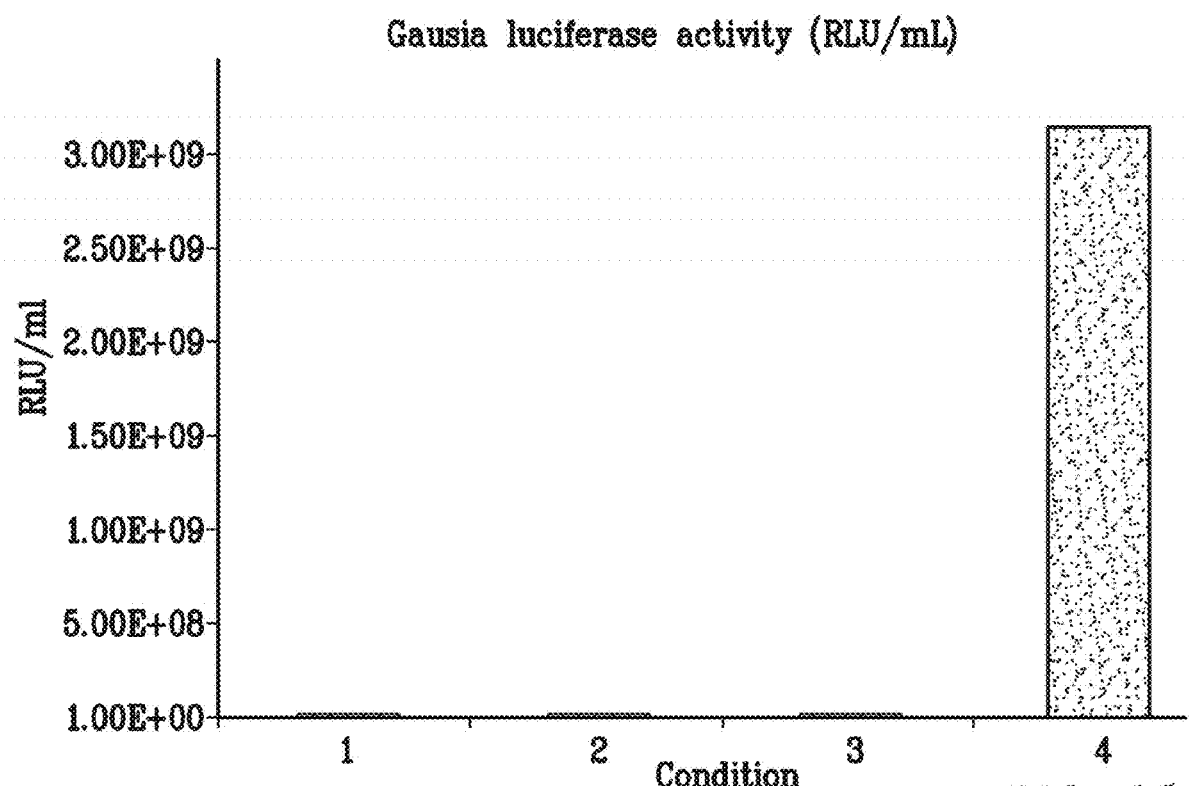
Figure 6B:
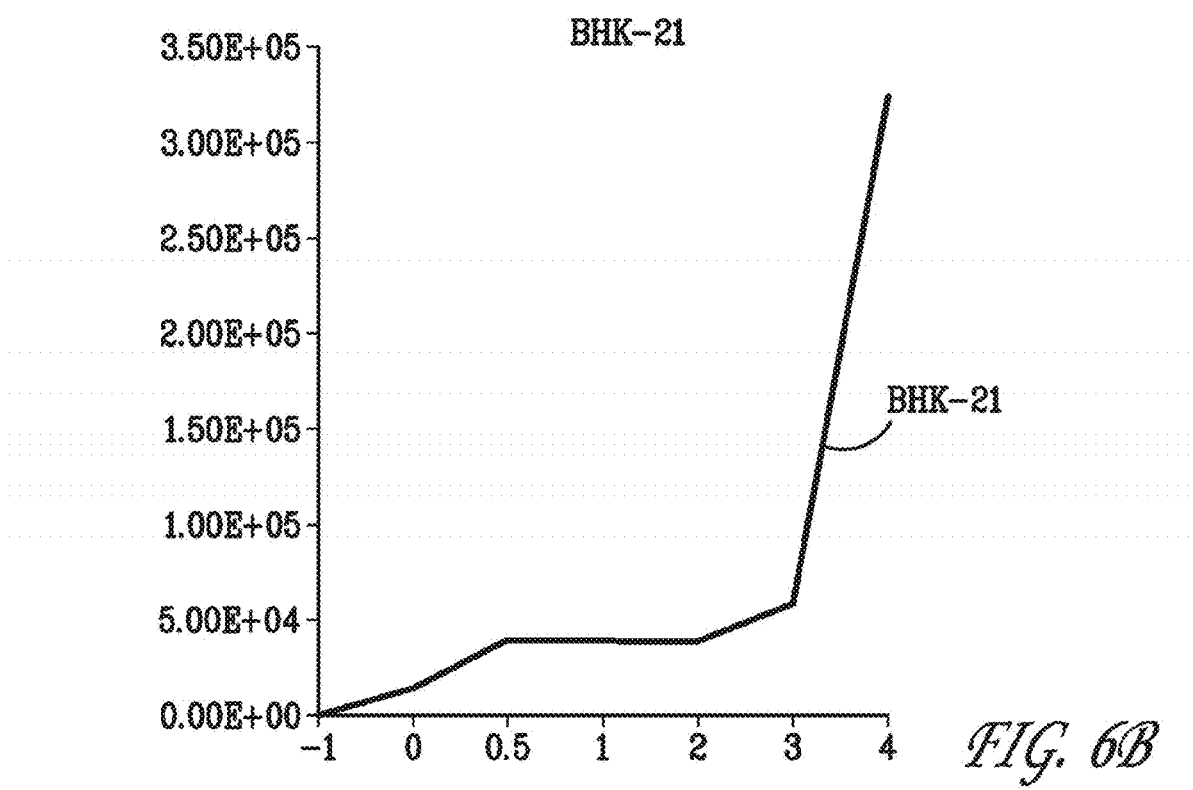

Another embodiment of the description is a method of producing the VLP described herein, comprising the steps of co-transforming a eukaryotic cell with a first vector comprising a polynucleotide sequence encoding the alphavirus replicon, wherein the alphavirus replicon includes the polynucleotide of interest, a second vector comprising a polynucleotide sequence encoding the retroviral gag protein, and a third vector comprising a polynucleotide sequence encoding the fusogenic envelope protein; culturing the co-transformed cell under conditions suitable to cause each vector to produce its encoded product, thereby producing the VLP, and isolating the VLP from the cell, wherein neither the vectors nor the cell contain any alphavirus structural protein genes.

Another embodiment of the description is kit comprising a first vector comprising a polynucleotide sequence encoding an alphavirus replicon, wherein the alphavirus replicon includes the polynucleotide of interest; a second vector comprising a polynucleotide sequence encoding the retroviral gag protein; and a third vector comprising a polynucleotide sequence encoding the fusogenic envelope protein, such as VSV-G. In some embodiments, the vectors provided with the kits do not include alphavirus structural protein genes. Alternatively, in some embodiments one or more of the alphavirus replicon, retroviral gag protein and fusogenic envelope protein may be encoded by the same vector.

Another embodiment of the description is a method of expressing the recombinant polynucleotide in a eukaryotic cell comprising treating a cell with the VLP described herein.

Another embodiment of the description is a method of delivering the recombinant polynucleotide described herein to a subject, comprising administering to said subject the VLP described herein.

Another embodiment of the description is a method of treating or preventing a disease or a disorder in a subject, comprising administering to a subject the VLP described herein. Preferably, expression of the gene of interest supplements deficient expression of an endogenous gene by said subject.

Another embodiment of the description is a pharmaceutical composition comprising the VLP described herein.

Another embodiment of the description is a eukaryotic cell produced by treating the cell with a VLP described herein.

To produce VLPS of this sort several components may be produced by transfecting or nucleofecting one or more vectors encoding these components into a cell line for in vitro production. In some embodiments, these components are encoded by separate vectors to reduce the likelihood that the resulting VLP will be replication competent. For example, a multi-vector system may be used where one vector encodes the genetic material, such as an alphavirus-based RNA polynucleotide, to be packaged by the VLP; another encodes the structural proteins of the VLP, such a gag protein; and another vector encodes a fusion protein, such as VSV-G, to facilitate fusion of the VLP to the membrane of a target cell. The alphavirus-based RNA polynucleotide can be derived from any alphavirus. In some embodiments, the RNA polynucleotide is derived from Sindbis virus and encodes Sindbis virus nonstructural protein. In some embodiments, the RNA polynucleotide is derived from Venezuelan equine encephalitis virus (VEEV) and encodes VEEV nonstructural proteins. However, other alphavirus nonstructural proteins may suffice for the RNA construct described herein. Suitable alphaviruses include Aura virus, Babanki virus, Barmah Forest virus, Bebaru virus, Cabassou virus. Chikungunya virus, Eastern equine encephalitis virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus, Salmon pancreas disease virus, Semliki Forest virus, Southern elephant seal virus, Tonate virus, Trocara virus, Una virus, Venezuelan equine encephalitis virus, Western equine encephalitis virus, and Whataroa virus.

Also described herein are cells comprising the vectors described to produce VLPs. These cells may be used to produce the VLPs described herein by transcribing or expressing the polynucleotides of the vectors. For instance, a mammalian cell transfected with a vector having a polynucleotide sequence encoding an alphavirus RNA construct having a gene or polynucleotide of interest and a packaging signal, a vector encoding a retroviral gag protein, and a vector encoding a viral fusion protein could produce a VLP having the expressed viral fusion protein on its surface with one or two copies of the encoded alphavirus RNA construct housed inside the VLP. Furthermore, because none of these vectors encode alphavirus structural proteins the possibility of creating an infectious virus is substantially reduced compared to systems that do include alphavirus structural proteins.

VLPs produced using the vectors and cells are also described herein. The VLPs described herein will have four general characteristics: they will comprise one or two RNA molecules encoding an alphavirus replicon, and optionally a protein of interest; they will have a viral core comprising a retroviral gag protein, or, in some embodiments, a gag fusion protein; they will have a surface protein to facilitate fusion with a cell, and they will not contain a polynucleotide that encodes an alphavirus structural protein.

The VLPs described herein may be produced in a variety of ways, as will be apparent to those skilled in the art based on the provided disclosure. The commonality to these various methods is the expression of the described vectors in a cell capable of expressing the necessary proteins (gag and a fusion protein) and producing the alphavirus-based RNA replicon.

BRIEF DESCRIPTION OF THE DRAWINGS

FIGS. 1A, 1B and 1C illustrate the elements of the three vectors exemplified herein. FIG. 1A shows the plasmid pCMV-Sin Rep-protein of interest-2 (POI-2), which is a Sindbis virus-based replicon. FIG. 1B shows the plasmid pGAG-protein of interest-1 (POI-1), which encodes a retroviral gag protein. FIG. 1C shows the plasmid pEnvelope, which encodes the viral fusion protein, such as VSV-G.

FIG. 2 schematically shows an example of a vector according to the description corresponding to the plasmid depicted in FIG. 1A. The DNA sequence of the vector is provided in the Sequence Listing, appended hereto.

FIG. 3 schematically represents how the transducing VLPs described herein are produced.

FIGS. 4A, 4B and 4C depict the results of three separate VLP transduction experiments. FIG. 4A shows cells transduced with a GFP-expressing Sindbis virus replicon packaged into VLPs obtained from supernatants collected from Baby Hamster Kidney (BHK)-21 cells transfected with all three plasmids; FIG. 4B shows the absence of GFP expression in cells incubated with cell supernatants collected from BHK-21 cells nucleofected with only the pCMV-Sin Rep-POI-2 and pGAG-POI-1 plasmids in the absence of envelope protein. FIG. 4C shows transduction of human embryonic kidney (HEK293T) cells to demonstrate that the constructed VLPs can transduce human cells.

FIGS. 5A, 5B, 5C and 5D show that the VLPs described herein can successfully transduce cells following storage at 4° C. for 1 hour (FIG. 5A), 2 days (FIG. 5B), 4 days (FIG. 5C), and 8 days (FIG. 5D).

FIGS. 6A and 6B show the expression levels of *Gaussia* luciferase by cells transduced with VLPs having a VEEV replicon capable of expressing the *Gaussia* luciferase gene (FIG. 6A, condition 4). Conditions 1, 2, and 3 of FIG. 6A show expression of *Gaussia* luciferase by cells transduced with VEEV replicons having no exogenous gene (condition 1) or with a gene encoding GFP (conditions 2 and 3). FIG. 6B provides an illustration of the expression kinetics of the luciferase protein during the first 4 hours after transduction.

FIGS. 7A and 7B illustrate the genetic process by the cre/lox system can be used to alter gene expression in a cell by delivering cre recombinase to a cell via transduction with a VLP having a VEEV replicon with the cre recombinase gene (FIG. 7A). The gene expression profile for a cell line engineered to express GFP in the absence of cre recombinase and RFP in the presence of cre recombinase is shown before and after (days 5, 6, and 7) transduction with a VLP carrying a replicon capable of expressing cre recombinase. FIG. 7B shows results of delivering functional cre recombinase (red cells) to cells engineered to express GFP in the absence of cre recombinase.

Figure 8:
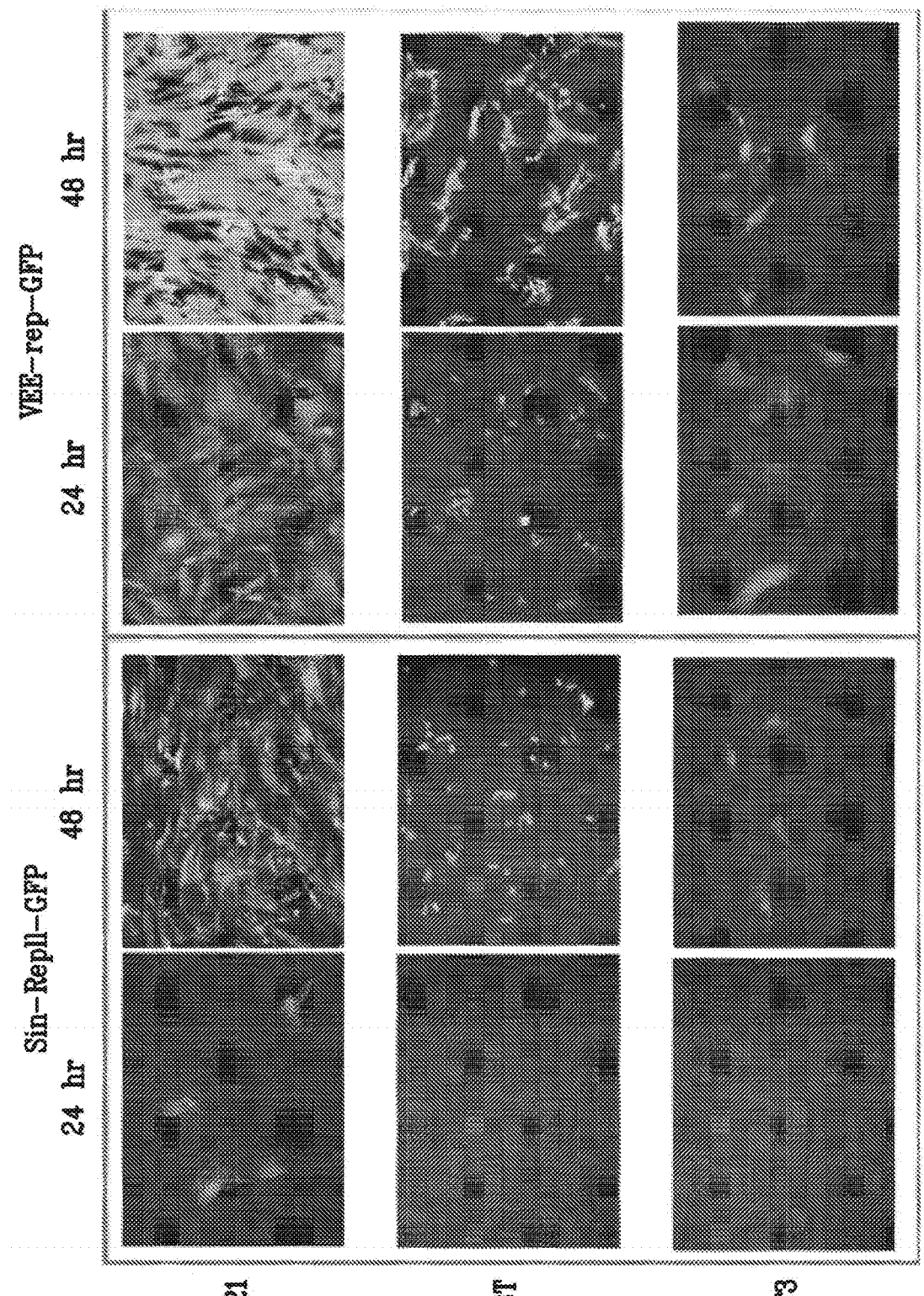

FIG. 8 depicts expression of GFP following transduction of BHK-21 cells, 293T cells, or NIH3T3 cells with VLPs having either a Sindbis virus or VEEV-based replicon capable of expressing GFP. 24 and 48-hour time points are shown for all samples.

Figure 9A:
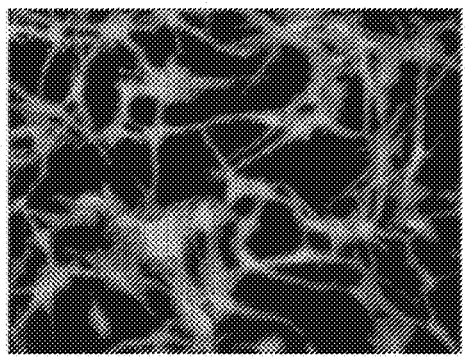
Figure 9B:
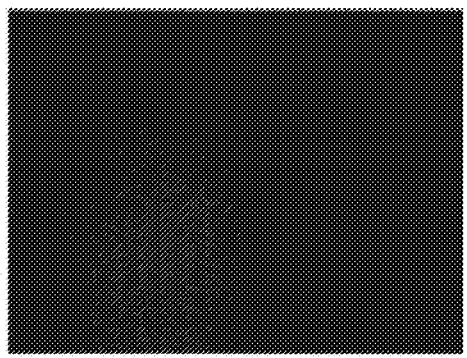
Figure 9C:
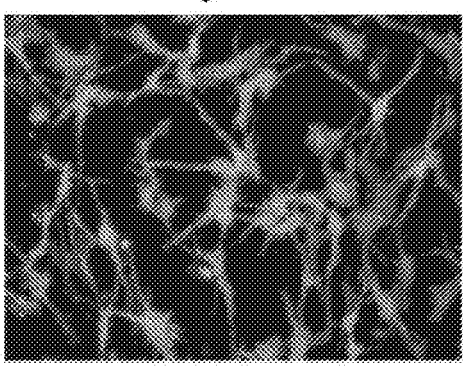
Figure 9D:
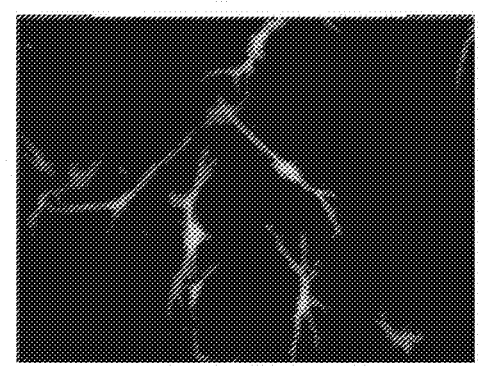
Figure 9E:
Figure 9F:
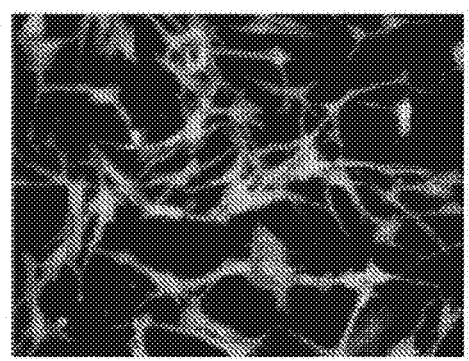
Figure 9G:
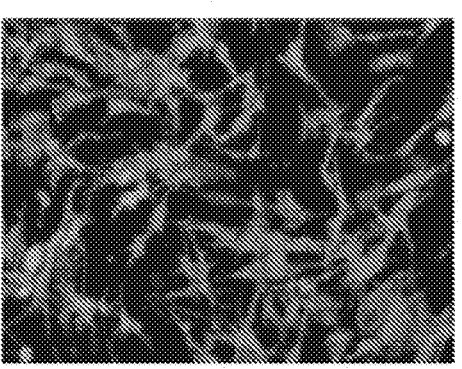

FIGS. 9A, 9B, 9C, 9D, 9E, 9F, and 9G illustrate functional packaging of non-coding RNA into VLPs. Cells transduced with VLPs containing: VEE-rep-GFP (encoding GFP) (FIG. 9A), VEE-Rep miGFP (encoding microRNA for GFP) (FIG. 9B), VEERep-GFP and VEERep miGFP (simultaneous transduction) (FIG. 9C), VEERep-GFP and VEERep miGFP (miRNA transduction occurred 4 hours prior to GFP transduction) (FIG. 9D), VEE-rep-Cre (used in place of scrambled miRNA to demonstrate specificity of miRNA) (FIG. 9E), VEE-Rep-GFP and VEE-Rep-Cre (simultaneous transduction) (FIG. 9F), or VEERep-Cre, incubation of cells for 4 hr prior to transduction with VLPs containing VEE-Rep-GFP (FIG. 9G).

FIGS. 10A and 10B show a schematic representation of an alphavirus replicon having two different genes (encoding either HLA-DR1 or CD80) the expression of which can occur in the same cell (FIG. 10A). Images of cells expressing both proteins following transduction with a VLP having a replicon shown in FIG. 10A are provided in FIG. 10B, where HLA-DR1 expression is visualized using immunospecific labeling with FITC (green) and CD80 is visualized with immunospecific labeling with phycoerythrin (red); a merged image is also shown to illustrate coexpression in the same cells.

Figure 11:
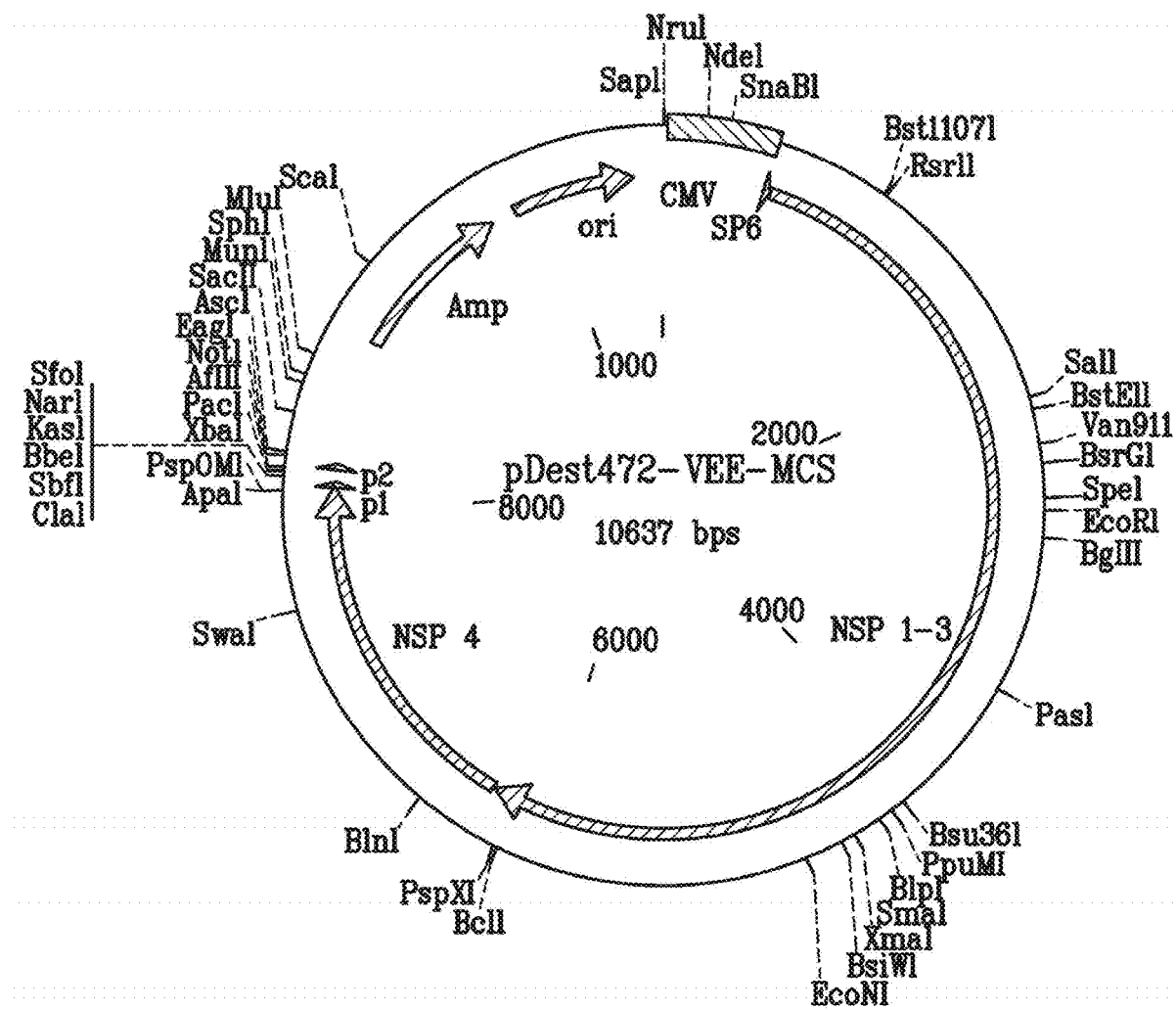

FIG. 11 provides a schematic representation of pDest472-VEE-MCS.

Figure 12:
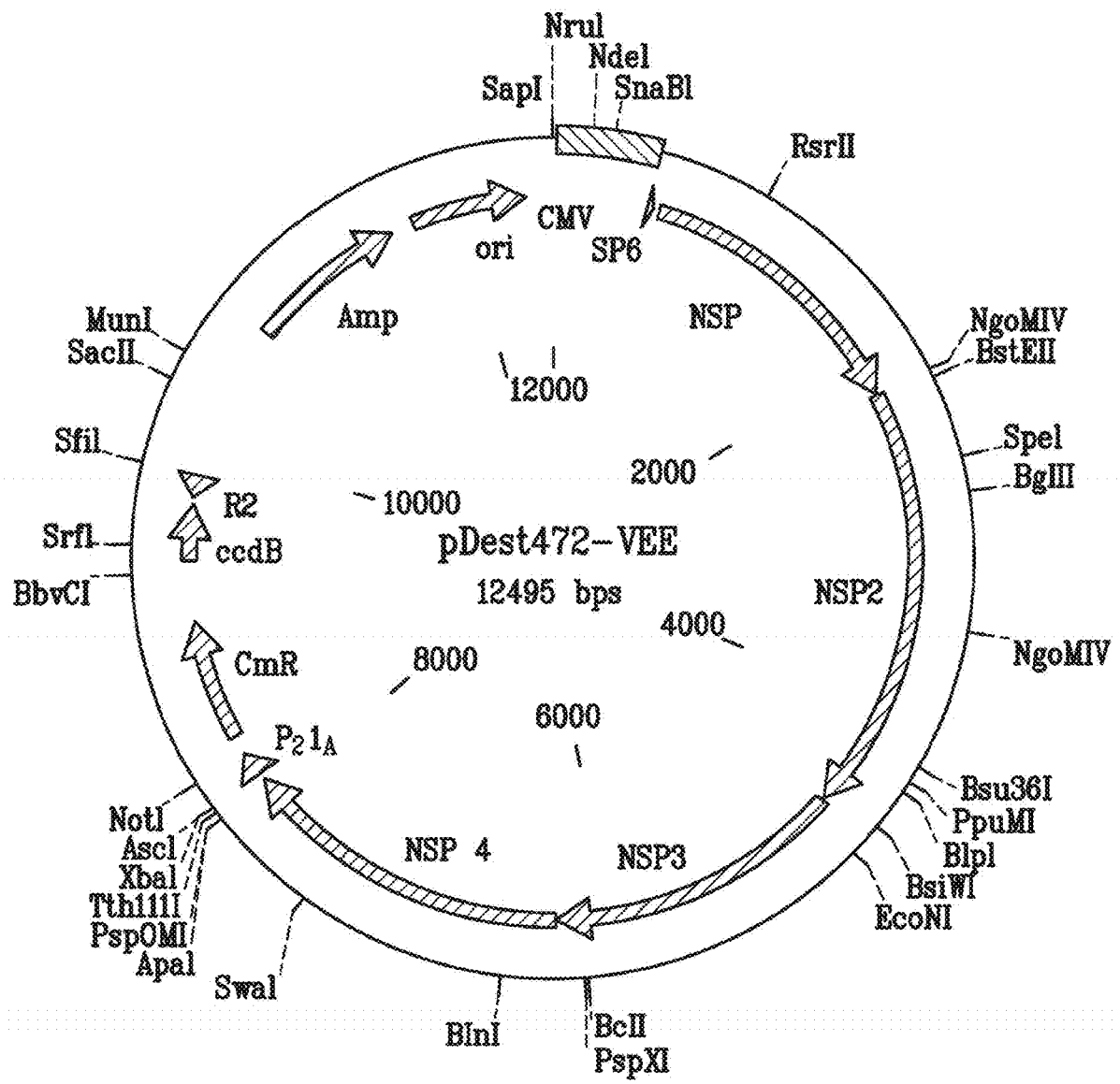

FIG. 12 provides a schematic representation of pDest472-VEE.

DETAILED DESCRIPTION OF ILLUSTRATIVE EMBODIMENTS

Various alphavirus-based expression vectors for transgene expression in target cells have been described (Xiong C., et al., 1989, Science 1188-91; and Bredenbeek P. et al., 1993, J. Virol. 6439-46). For safety considerations these expression systems usually comprise two plasmids. One plasmid contains the coding sequence of the viral replicon (i.e., non-structural proteins) and an internal promoter and transgene coding region, while the second plasmid encodes the viral structural genes. These plasmids are used to generate mRNA in vitro, which is then electroporated into host cells to generate one-round infectious virus particles. These viral particles are then used to infect target cells for transgene expression. These particles raise safety concerns, however, because recombination between the sequence elements encoding the non-structural and the structural viral elements can yield replication-competent alphavirus particles having the ability to mediate a significant cytopathic effect in vivo.

A possible solution to this problem is to use unrelated VLPs to deliver alphavirus replicons to the cytoplasm of mammalian cells where they can replicate autonomously and express genes of interest without any nuclear involvement. These VLPs can be produced using three vectors. The first vector comprises the coding sequence for the alphavirus replicon under the control of a mammalian promoter (e.g., CMV), a retroviral-specific RNA packaging signal, and a gene or polynucleotide of interest. The gene may express a protein with therapeutic or research applications, or a shRNA or other regulatory nucleic acid. The second vector comprises retroviral Gag. The third vector would provide the suitable envelope glycoprotein for infection of target cells.

Upon co-transfection into an appropriate packing cell line, RNA molecules transcribed from the cellular promoter present in the first vector will be packaged into VLPs produced from the second vector. These VLPs can deliver the alphavirus-based replicon to a target cell based on the envelope glycoprotein present in the VLPs. Once inside the cell, the host translational machinery will translate the introduced alphavirus RNA and produce alphavirus replication proteins, which will in turn amplify the RNA and express the gene or polynucleotide of interest. Mutant replicons such as the one described above can greatly prolong the duration of expression with minimal impact on the host cell. Moreover, DNA encoding genes for alphavirus structural elements will be absent in the target cell, so the safety of the proposed system is greatly enhanced.

Described herein are compositions relating to VLPs and methods for making and using the described VLPs. The described compositions include VLPs, and vectors and cells used to produce the described VLPs. The related methods described herein relate to methods of producing the VLPs, methods of transducing cells using the VLPs, and methods of producing a protein or polynucleotide of interest in a target cell using the VLPs described herein. Also described are alphavirus-based replicons that allow for expression of proteins or polynucleotides of interest in a target cell without the risk of viral infection.

Definitions

When the terms "one," "a," or "an" are used in this disclosure, they mean "at least one" or "one or more," unless otherwise indicated.

The term "fusogenic protein" as used herein is meant to refer to a protein that can induce the fusion of the plasma membrane derived envelope of the VLP to the membrane of the recipient cell.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Replicon" as used herein refers to a polynucleotide having the genetic elements necessary to facilitate replication of its sequence and while also being capable of undergoing translation.

"Virus-like particle" (VLP), as used herein, refers to a structure resembling a virus particle. In preferred embodiments, a VLP contains at least one fusogenic protein displayed on the surface of the particle. A virus-like particle in accordance with the invention lacks all or part of the replicative components of the viral genome. Typically, a virus-like particle in accordance with the invention does not carry genetic information encoding for the proteins of the virus-like particle.

Vectors

Described herein are vectors for use in producing VLPs carrying an alphavirus-based replicon that does not encode alphavirus structural proteins. To produce VLPS of this sort, several components may be produced by transfecting or nucleofecting one or more vectors encoding these components into a cell line for in vitro production. In some embodiments, these components are encoded by separate vectors to reduce the likelihood that the resulting VLP will be replication competent. For example, a multi-plasmid system may be used where one plasmid encodes the genetic material, such as an RNA polynucleotide encoding Sindbis virus or VEEV nonstructural proteins, to be packaged by the VLP; another encodes the structural proteins of the VLP, such as gag; and another plasmid encodes a fusion protein, such as VSV-G, to facilitate fusion of the VLP to the membrane of a target cell.

The vectors encoding the genetic material to be packaged by a host cell can take a variety of forms, such as selectable or inducible plasmids, but generally have some common characteristics. For example, vectors encoding an RNA alphavirus-based replicon described herein may include a promoter sequence, a retroviral packaging signal sequence, translation initiation sequences, nonstructural alphavirus proteins, a cloning site for inserting a gene or polynucleotide of interest, an inserted gene or polynucleotide of interest, a 3' untranslated region, and a poly-adenosine tail segment.

In some embodiments the described vectors include a promoter element that allows for segments of the vector to be transcribed by a host cell. In some embodiments the vector sequence may be transcribed into RNA to be packaged into a VLP. In most embodiments of the described vectors, the promoter sequence will be located upstream of all of the translatable elements included within the vector (see for example, FIG. 1(a) illustrating the location of the cytomegalovirus promoter "pCMV"). In some embodiments described herein the promoter sequence will be derived from a virus, such as cytomegalovirus (CMV), or simian virus 40 (SV40). Numerous other promoter sequences are well known to those skilled in the art and their use with the vectors described herein would be apparent based on the description provided.

In some embodiments the described vectors encoding the genetic material to be packaged by a host cell can include a polynucleotide sequence that encodes a retroviral packaging signal sequence (also known as a psi ($\Psi$) element) to allow one or two copies of the RNA sequence transcribed from the vector to be packaged into a VLP particle formed in a host cell. Most, if not all, retroviruses have a packaging sequence of this nature, thus these sequences, and their incorporation into the described vectors, will be readily apparent to those skilled in the art. In some embodiments the vectors described herein include a polynucleotide sequence that encodes a retroviral packaging sequence derived from Rous sarcoma virus. Moloney murine leukemia virus, simian immunodeficiency virus (SIV), HIV, human T-lymphotropic virus, and the like. In a particular embodiment, the retroviral packaging sequence is derived from Rous sarcoma virus. Alternatively, the retroviral packaging sequence is derived from murine leukemia virus.

Another aspect of the vectors encoding the genetic material to be packaged by a host cell described herein are translation initiation sequences, which allow the RNA sequence encoded by the vector to be translated in a host cell. In some embodiments the described translation initiation sequences may be capable of allowing for expression of alphavirus-based nonstructural proteins, which can replicate the RNA sequence carried by the described VLPs once it is delivered to the host cell. In some embodiments, the described translation initiation sequences may be capable of allowing for expression of a gene of interest. In some embodiments the translation initiation sequence may allow for the gene of interest to be translated by host cell translation complexes. In some embodiments the translation initiation sequences described herein may be derived from an alphavirus, such as Sindbis virus or VEEV. In other embodiments the translation initiation sequences may be derived from other genes, such as virus genes known to have translation initiation sequences capable of initiating translation of an RNA sequence by mammalian translation complexes. Alternatively, the translation initiation sequences may be derived from other genes, such as the native translation initiation sequence of the gene of interest inserted into the described alphavirus replicon. In some embodiments the translation initiation sequences described herein may be located at more than one location in the packaged RNA molecule, and thus may be encoded one or more times by the described vectors. For example, it may be desirable to translate the described Sindbis or VEEV nonstructural proteins separately from a gene of interest encoded by the package RNA molecule. In such an instance, both the polynucleotide(s) encoding the nonstructural proteins and the polynucleotide encoding the protein of interest will have separate translation initiation sequences located 5' of their position in the vector and packaged RNA. Based on this description, those skilled in the art will understand that a variety of translation initiation sequences capable of promoting the translation of RNA in a mammalian cell may be incorporated to the described VLP-packaged RNAs described herein.

The vectors encoding genetic material to be packaged by a host cell may also include polynucleotides that encode nonstructural alphavirus proteins, such as nonstructural proteins from Sindbis virus or VEEV. For example, in some embodiments the described vectors may include polynucleotides that encode one or more Sindbis virus nonstructural proteins. In some embodiments the described vectors may include polynucleotides that encode one or more VEEV nonstructural proteins. In some embodiments described vectors may include polynucleotides that encode the Sindbis virus or VEEV nonstructural protein NSP1. In some embodiments described vectors may include polynucleotides that encode the Sindbis virus or VEEV nonstructural protein NSP2. In some embodiments described vectors may include polynucleotides that encode the Sindbis virus or VEEV nonstructural protein NSP3. In some embodiments described vectors may include polynucleotides that encode the Sindbis virus or VEEV nonstructural protein NSP4. In some embodiments described vectors may include polynucleotides that encode the Sindbis virus or VEEV nonstructural proteins NSP1, NSP2, NSP3, and NSP4. In some embodiments the polynucleotide of the described vector that encodes the alphavirus nonstructural proteins will be derived from the corresponding genomic sequence of an alphavirus genome, such as that of Sindbis virus or VEEV. In some embodiments, the polynucleotides encoding the alphavirus nonstructural proteins are void of any polynucleotides that encode the alphavirus structural proteins, regardless of whether the structural proteins are from the same or a different alphavirus than the nonstructural protein sequences present.

The vector described herein for incorporating genetic material to be packaged by a host cell may also contain a polynucleotide of interest that may be expressed in a host cell transduced by a VLP carrying the genetic material encoded by the vector. In some embodiments the described vectors may encode an RNA polynucleotide sequence to be packaged into a VLP, which can then be delivered to a host cell by VLP-mediated transduction of the cell. Once the RNA polynucleotide sequence has been delivered to the target cell a polynucleotide of interest encoded by the RNA may provide for expression of a protein of interest. Accordingly, the vectors described herein are designed to encode an RNA for packaging into a VLP that can express a gene of interest once inside a target cell. Therefore, in some embodiments the described vectors will include a polynucleotide sequence of interest. In some embodiments of the described vector, the polynucleotide sequence of interest may encode a protein of interest. For example, the polynucleotide sequence of interest may encode GFP in some embodiments and serve a detectable marker of viral transduction of a target cell. In another embodiment, the polynucleotide sequence of interest may encode a functional version of a protein endogenous to the target cell. In another embodiment, the polynucleotide sequence of interest may encode a functional version of a protein endogenous to the target subject. In another embodiment, the polynucleotide sequence of interest may encode a protein that is foreign to the target cell. In another embodiment, the polynucleotide sequence of interest may encode a protein that is foreign to the target subject. In some embodiments the polynucleotide sequence of interest may encode a protein capable of having a therapeutic effect on a target cell. In some embodiments the polynucleotide sequence of interest may encode a protein capable of having a therapeutic effect on a target subject. In an alternative embodiment the polynucleotide sequence of interest may server as an interfering RNA molecule and function to regulate endogenous gene expression in a host cell. For example, in some embodiments the polynucleotide sequence of interest may comprise a sequence that provides for the formation of an RNA hairpin loop to initiate RNA interference. In addition, the polynucleotide of interest could be a positive or negative sense strand of RNA that can be transcribed by the RNA-dependent RNA polymerase complex formed by the alphavirus nonstructural proteins encoded by the packaged RNA molecule. Since this RNA-dependent RNA polymerase can transcribe RNA in the positive-sense and negative-sense directions, an interfering RNA sequence, such as a miRNA or shRNA, may be inserted into the packaged RNA replicon and can be designed to encode an interfering polynucleotide in either direction. Those of skill in the art will appreciate the therapeutic characteristic of this aspect of the described transduction system, as it can allow for expression of selected proteins in a subject. In accordance with this aspect of the described vector, a cloning site having one or more restriction endonuclease sites may also be included in the vector, to facilitate insertion of a polynucleotide sequence of interest.

Another vector useful in the production of the VLPs described herein is a vector that encodes a virus structural protein. One such class of proteins is the retroviral group-specific antigen (gag) protein. The gag protein is the core structural protein of retroviruses and, in some instances, is capable of forming enveloped virus cores when expressed in eukaryotic cells. This property makes gag proteins particularly useful in the production of VLPs, because they can form the basic structural aspect of the particle and allow for packaging of RNA associated with a retroviral packaging signal sequence. Accordingly, described herein are vectors that include a polynucleotide that encodes a retroviral gag protein. In some embodiments, the described vectors include a polynucleotide that encodes a retroviral gag protein and a promoter polynucleotide sequence that allows for the gag gene sequence to be transcribed into mRNA by host cell RNA polymerase. In one embodiment, the promoter polynucleotide sequence is derived from a virus, such as SV40 or CMV. In some embodiments, the vector will further include a polynucleotide that encodes a protein of interest. Those skilled in the relevant art will understand that a polynucleotide sequence of a gag protein from any retrovirus may be used to produce the vectors and VLPs described herein. In some embodiments the polynucleotide sequence encoding the gag protein may be derived from Rous sarcoma virus. In some embodiments the polynucleotide sequence encoding the gag protein may be derived from murine leukemia virus. In some embodiments the polynucleotide sequence encoding the gag protein may be derived from SIV. In some embodiments the polynucleotide sequence encoding the gag protein may be derived from human T-lymphotropic virus.

Another vector useful in the production of the VLPs described herein is a vector that encodes a protein to mediate fusion between the VLP envelope and a host cell. A class of proteins suitable for this purpose is viral fusion proteins, which facilitate virus infection of cells by allowing an enveloped virus to fuse its membrane with that of a host cell. Many of viral fusion proteins also have known, or suspected, cellular receptor proteins that may allow for targeting of selected cell types, or in cases of more ubiquitous receptors, such as sialic acid for influenza virus, more generalized targeting may be desired. In some instances, viral fusion proteins work in conjunction with viral attachment proteins, ligands for cellular receptor, a receptor for a cell ligand, or accessory proteins, thus proteins of this sort may also be encoded by the described vectors, in addition to, or also by, the vector encoding a viral fusion protein. Alternatively, in some embodiments a viral fusion protein from one virus may be encoded by the described vector along with a viral attachment protein of another virus, a ligand of a cellular receptor, a receptor of a cell ligand, or an accessory protein to facilitate, or direct, targeting of a VLP to a desired cell type. In some embodiments the viral fusion protein, viral attachment protein, ligand of a cellular receptor, receptor of a cell ligand, or accessory protein will be a type-I membrane protein, which will allow the extracellular domain of the protein to be oriented extracellularly when present on the cell surface. This will also allow the fusion protein to be correctly oriented following budding of a VLP from a packaging cell. Expression of such proteins in a cell will typically result in the cell surface being coated with the proteins, so that budding of a VLP from any part of the cell membrane will provide the VLP with some amount of the protein(s) on its surface. In some embodiments, the described vectors include a polynucleotide that encodes a viral fusion protein and a promoter polynucleotide sequence that allows for the fusion protein gene sequence to be translated into mRNA by host cell RNA polymerase. In one embodiment, the promoter polynucleotide sequence is derived from a virus, such as SV40 or CMV. In some embodiments, the described vectors include a polynucleotide that encodes a viral attachment protein and a promoter polynucleotide sequence that allows for the attachment protein gene sequence to be translated into mRNA by host cell RNA polymerase. In one embodiment, the promoter polynucleotide sequence is derived from a virus, such as SV40 or CMV. In some embodiments the vectors described herein include a polynucleotide that encodes a vesicular stomatitis virus G protein. In some embodiments the vectors described herein include a polynucleotide that encodes the influenza hemaglutinin protein. In some embodiments the vectors described herein include a polynucleotide that encodes the influenza neuraminidase protein. In some embodiments the vectors described herein include a polynucleotide that encodes the respiratory syncytial virus fusion protein. In some embodiments the vectors described herein include a polynucleotide that encodes the rotavirus VP7 protein. Other such fusion proteins will be apparent to those skilled in the art based on desired tropism or cell target of the associated virus.

Cells Expressing the Described Vectors

Provided herein are cells comprising the vectors described to produce VLPs. These cells may be used to produce the VLPs described herein by transcribing or expressing the polynucleotides of the vectors. For instance, a mammalian cell transfected with a vector having a polynucleotide sequence encoding an alphavirus RNA construct having a gene or polynucleotide of interest and a packaging signal, a vector encoding a retroviral gag protein, and a vector encoding a viral fusion protein could produce a VLP having the expressed viral fusion protein on its surface with one or two copies of the encoded alphavirus RNA construct housed inside the VLP. Furthermore, because none of these vectors encode alphavirus structural proteins the possibility of creating an infectious virus is substantially reduced compared to systems that do include alphavirus structural proteins.

The described cells may be any eukaryotic cell capable of transcribing, and where necessary (such as in the case of the gag and fusion proteins), translating the polynucleotides of the described vectors. The cells will likely be mammalian cells in many embodiments. For example, rodent cells, such as murine, hamster (CHO or BHK-21), or rat cells could be used to express the described vectors; canine cells, such as Madin Darby canine kidney cells, could be used to express the described vectors; primate cells, such as vero cells, could be used to express the described vectors; and human cells, such as HEK293T cells (human kidney), Hep-2 cells (human airway), Caco-2 (intestine), HeLa (epithelium), and other such cell lines known in the art, could be used to express the described vectors. In some embodiments the described cells can be transfected and selected, using standard transfection and selection methods known in the art, to stably comprise one or more of the described vectors.

In some embodiments the cell lines described herein will contain a vector comprising a polynucleotide sequence encoding an alphavirus replicon wherein the alphavirus replicon encodes a protein of interest, a vector comprising a polynucleotide sequence encoding a gag protein, and a vector comprising a polynucleotide sequence encoding a heterologous fusogenic envelope protein, wherein neither the vectors nor the cell contain a gene encoding an alphavirus structural protein. In some embodiments the alphavirus replicon may be derived from Sindbis virus or VEEV. In some embodiments the alphavirus replicon may have polynucleotide sequences that encode Sindbis virus or VEEV nonstructural proteins NSP1, NSP2, NSP3, NSP4, and a retroviral packaging signal. In some embodiments the retroviral packaging signal may be derived from either Rous sarcoma virus or murine leukemia virus. In some embodiments the polynucleotide sequence encoding the gag protein is derived from Rous sarcoma virus. In some embodiments the polynucleotide sequence encoding the heterologous fusogenic envelope protein encodes VSV-G.

Virus-like Particles

VLPs produced using the vectors and cells are also described herein. The VLPs described herein will have four general characteristics: they will comprise one or two RNA molecules encoding an alphavirus replicon, and optionally a protein of interest; they will have a viral core comprising a retroviral gag protein, or, in some embodiments, a gag fusion protein; they will have a surface protein to facilitate fusion with a cell, and they will not contain a polynucleotide that encodes an alphavirus structural protein.

The VLPs described herein will be useful in transducing cells in order to express a protein of interest therein. Accordingly, the described VLPs may incorporate one or two alphavirus-based RNA polynucleotides capable of encoding a protein of interest. To facilitate translation of the RNA sequence some embodiments of the described packaged RNA may include translation initiation sequences as described herein. In some embodiments the RNA sequence incorporated into the VLP will include a retroviral packaging sequence that will facilitate inclusion of the RNA into a forming VLP. In some embodiments the retroviral packaging sequence is derived from Rous sarcoma virus, Moloney murine leukemia virus, simian immunodeficiency virus (SIV). HIV, human T-lymphotropic virus, and the like. In a particular embodiment, the retroviral packaging sequence is derived from Rous sarcoma virus. Alternatively, the retroviral packaging sequence may be derived from murine leukemia virus. In addition, the RNA sequences included in the VLP may be capable of encoding nonstructural alphavirus proteins. For example, in some embodiments the packaged RNA may encode one or more Sindbis virus or VEEV nonstructural proteins. In some embodiments the packaged RNA may encode the Sindbis virus or VEEV nonstructural protein NSP1. In some embodiments the packaged RNA may encode the Sindbis virus or VEEV nonstructural protein NSP2. In some embodiments the packaged RNA may encode the Sindbis virus or VEEV nonstructural protein NSP3. In some embodiments the packaged RNA may encode the Sindbis virus or VEEV nonstructural protein NSP4. In some embodiments the packaged RNA may encode the Sindbis virus or VEEV nonstructural proteins NSP1, NSP2, NSP3, and NSP4. The packaged RNA may also include the polynucleotide sequence of a protein of interest. For example, the polynucleotide sequence of interest may encode GFP in some embodiments and serve a detectable marker of viral transduction of a target cell. In another embodiment, the polynucleotide sequence of interest may encode a functional version of a protein endogenous to the target cell. In another embodiment, the polynucleotide sequence of interest may encode a functional version of a protein endogenous to the target subject. In another embodiment, the polynucleotide sequence of interest may encode a protein that is foreign to the target cell. In another embodiment, the polynucleotide sequence of interest may encode a protein that is foreign to the target subject. In some embodiments the polynucleotide sequence of interest may encode a protein capable of having a therapeutic effect on a target cell. In some embodiments the polynucleotide sequence of interest may encode a protein capable of having a therapeutic effect on a target subject. Those of skill in the art will appreciate the therapeutic characteristic of this aspect of the described VLPs, as they can allow for expression of selected proteins in a cell or subject.

The described VLPs may also comprise a viral gag protein to provide a viral core structure to the particle. The gag protein is the core structural protein of retroviruses and, in some instances, is capable of forming enveloped virus cores when expressed in eukaryotic cells. This property makes gag proteins particularly useful in the production of VLPs, because they can form the basic structural aspect of the particle and allow for packaging of RNA associated with a retroviral packaging signal sequence. Those skilled in the relevant art will understand that a gag protein from any retrovirus may be used to produce the vectors and VLPs described herein. In some embodiments the gag protein may be derived from Rous sarcoma virus. In some embodiments the gag protein may be derived from murine leukemia virus. In alternative embodiments the gag protein may be derived from SIV, HIV, human T-lymphotropic virus, or similar retrovirus.

Another component of the VLPs described herein is a protein to mediate fusion between the VLP envelope and a host cell. A class of proteins suitable for this purpose is viral fusion proteins, which facilitate virus infection of cells by allowing an enveloped virus to fuse its membrane with that of a host cell. Many of viral fusion proteins also have known, or suspected, cellular receptor proteins that may allow for targeting of selected cell types, or in cases of more ubiquitous receptors, such as sialic acid for influenza virus, more generalized targeting may be achieved. In some instances, viral fusion proteins may work in conjunction with viral attachment proteins, ligands of cellular receptors, receptors of cellular ligands, or accessory proteins, thus proteins of this sort may also be present on the VLP surface in addition to a viral fusion protein. Alternatively, in some embodiments the described VLPs may have a viral fusion protein from one virus and a viral attachment protein of another virus, a ligand of a cellular receptor, a receptor of a cellular ligand, or an accessory protein to facilitate, or direct, targeting of a VLP to a desired cell type. Similarly, the described VLPs may be produced to have more than one fusion protein in the VLP envelope, as this may facilitate fusion to a select variety of cell types. In some embodiments the VLP surface protein(s) will be a type-I membrane protein, which will allow the extracellular domain of the protein to be oriented extracellularly when present on the cell surface. This will also allow the fusion protein to be correctly oriented following budding of a VLP from a packaging cell. Expression of such proteins in a cell will typically result in the cell surface being coated with the proteins, so that budding of a VLP from any part of the cell membrane will provide the VLP with some amount of the fusion protein on its surface. In some embodiments the VLPs described herein include a vesicular stomatitis virus G protein (VSV-G) to mediate cell fusion. In some embodiments the VLPs described herein include an influenza hemagglutinin protein to mediate cell fusion. In some embodiments the VLPs described herein include an influenza neuraminidase protein to facilitate cell fusion. In some embodiments the VLPs described herein include respiratory syncytial virus fusion protein. In some embodiments the VLPs described herein include the rotavirus VP7 protein. Other such fusion proteins will be apparent to those skilled in the art based on desired tropism or cell target of the associated virus.

The VLPs described herein may comprise an alphavirus replicon, wherein the alphavirus replicon includes a polynucleotide of interest or encodes a protein of interest, retroviral gag protein, and heterologous fusogenic envelope protein; wherein the VLP does not contain an alphavirus structural protein gene. In some embodiments the alphavirus replicon of the VLP is derived from Sindbis virus or VEEV. For example, the VLPs described herein may have an alphavirus replicon encoding Sindbis virus or VEEV nonstructural proteins NSP 1, NSP2, NSP3, and NSP4. In some embodiments the retroviral packaging signal associated with the packaged RNA in the described VLPs is derived from either Rous sarcoma virus or murine leukemia virus. Based on this description, those skilled in the art will readily understand that the described VLPs may be modified to incorporate aspects of viruses that may facilitate VLP stability, RNA packaging, or cell entry. Such modifications should be understood to be within the scope of the disclosures provided herein.

Methods of Producing the Described VLPs

The VLPs described herein may be produced in a variety of ways, as will be apparent to those skilled in the art based on the provided disclosure. The commonality to these various methods is the expression of the described vectors in a cell capable of expressing the necessary proteins (gag and a fusion protein) and producing the alphavirus-based RNA replicon. Accordingly, a method of producing a VLP described herein may include co-transforming, transfecting, or nucleofecting a eukaryotic cell with a vector comprising a polynucleotide sequence encoding an alphavirus replicon, wherein the alphavirus replicon includes a polynucleotide of interest or encodes a protein of interest; a vector comprising a polynucleotide sequence encoding a retroviral gag protein; and a vector comprising a polynucleotide sequence encoding a heterologous fusogenic envelope protein; and culturing the co-transformed cell under conditions suitable to cause each vector to produce its encoded product, thereby producing a virus-like particle. In some embodiments the polynucleotide sequence encoding the alphavirus replicon may be derived from Sindbis virus or VEEV. In some embodiments the alphavirus replicon may have polynucleotide sequences that encode Sindbis virus or VEEV nonstructural proteins NSP1, NSP2, NSP3, NSP4, and a retroviral packaging signal. In some embodiments the retroviral packaging signal may be derived from either Rous sarcoma virus or murine leukemia virus. In some embodiments the polynucleotide sequence encoding the gag protein is derived from Rous sarcoma virus. In some embodiments the polynucleotide sequence encoding the heterologous fusogenic envelope protein encodes VSV-G.

Compositions and Methods of Administration

Described herein are compositions comprising at least one described VLP and a pharmaceutically acceptable carrier. Such compositions are useful, for example, for administration to subjects in need of expression of an exogenous protein or increased expression of a protein normally found in those of the same species as the subject. The compositions may be formulated as any of various preparations that are known and suitable in the art, including those described and exemplified herein. In some embodiments, the compositions are aqueous formulations. Aqueous solutions may be prepared by admixing the VLPs in water or suitable physiologic buffer, and optionally adding suitable colorants, flavors, preservatives, stabilizing and thickening agents and the like as desired. Aqueous suspensions may also be made by dispersing the VLPs in water or physiologic buffer with viscous material, such as natural or synthetic gums, resins, methylcellulose, sodium carboxymethylcellulose, and other well-known suspending agents.

The compositions may be formulated for injection into a subject. For injection, the compositions described may be formulated in aqueous solutions such as water or in physiologically compatible buffers such as Hanks's solution, Ringer's solution, or physiological saline buffer. The solution may contain one or more formulatory agents such as suspending, stabilizing or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions may be formulated for aerosolized delivery to a subject. For aerosol delivery, the compositions described may be formulated in aqueous solutions such as water or in physiologically compatible buffers such as Hanks's solution, Ringer's solution, or physiological saline buffer. The solution may contain one or more formulatory agents such as suspending, stabilizing or dispersing agents.

The compositions may be formulated in sustained release vehicles or depot preparations. Such long-acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The following examples are provided for illustrative purposes and are meant to enhance, not limit, the preceding disclosure.

Example 1

Production of an Alphavirus-Based Gene Expression System

An alphavirus gene expression system was designed to allow for VLP-mediated delivery an exogenous gene of interest (GOI) or protein of interest (POI) to a target cell with low risk of causing cytopathic viral infection. The expression system was designed using three vectors, which can be expressed in a packaging cell line to produce a transducing VLP. One vector codes for the alphavirus-based expression construct, another vector codes for a retroviral gag protein to facilitate VLP formation, and a third vector codes for a fusion protein to mediate VLP fusion to the host cell. In addition, the system was constructed to work without the need for alphavirus structural proteins being present.

Figure 2:
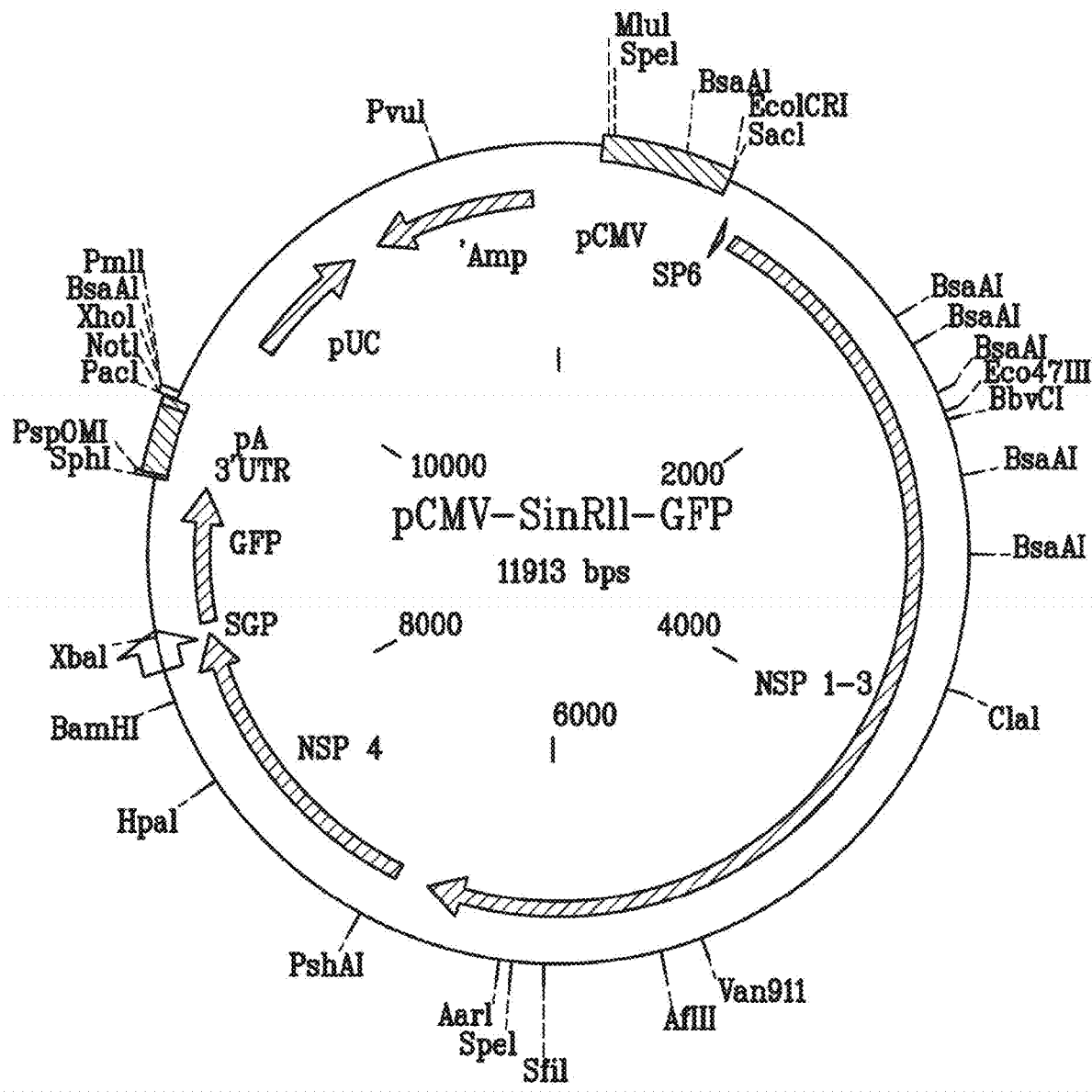

To accomplish this, an alphavirus-based DNA plasmid was produced having a cytomegalovirus promoter (CMV); followed by a retroviral packaging signal of respective retroviral packaging protein GAG; followed by a Sindbis or VEE virus genes encoding nonstructural proteins NSP1, NSP2, NSP3, and NSP4; and finally, one or more subgenomic promoter (SGP; a promoter for virus-encoded RNA-dependent RNA polymerase, resulting in the formation of mRNA) to drive expression of a of a gene of interest (GOI), consisting of a recombinant polynucleotide, and inserted into a multiple cloning site; a 3' untranslated region (URT); and a polyA tail. FIG. 2 shows an example of such an alphavirus-based DNA plasmid. In another version of this expression vector, the retroviral packaging signal (GAG) is omitted.

Figure 1B:
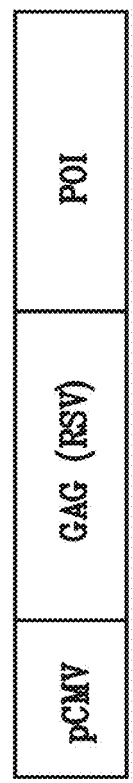
Figure 1C:
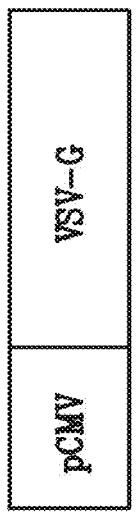

Another plasmid was constructed to encode a retroviral gag protein and a second, optional protein of interest (POI). A third plasmid was constructed to provide expression of a VSV-G viral fusion protein. A schematic of an embodiment of these plasmids is provided in FIG. 1A-1C, respectively. FIG. 1A shows pCMV-Sin Rep-POI-2, FIG. 1B shows pGAG-POI-1, and FIG. 1C shows pEnv for VSV-G.

Figure 3:
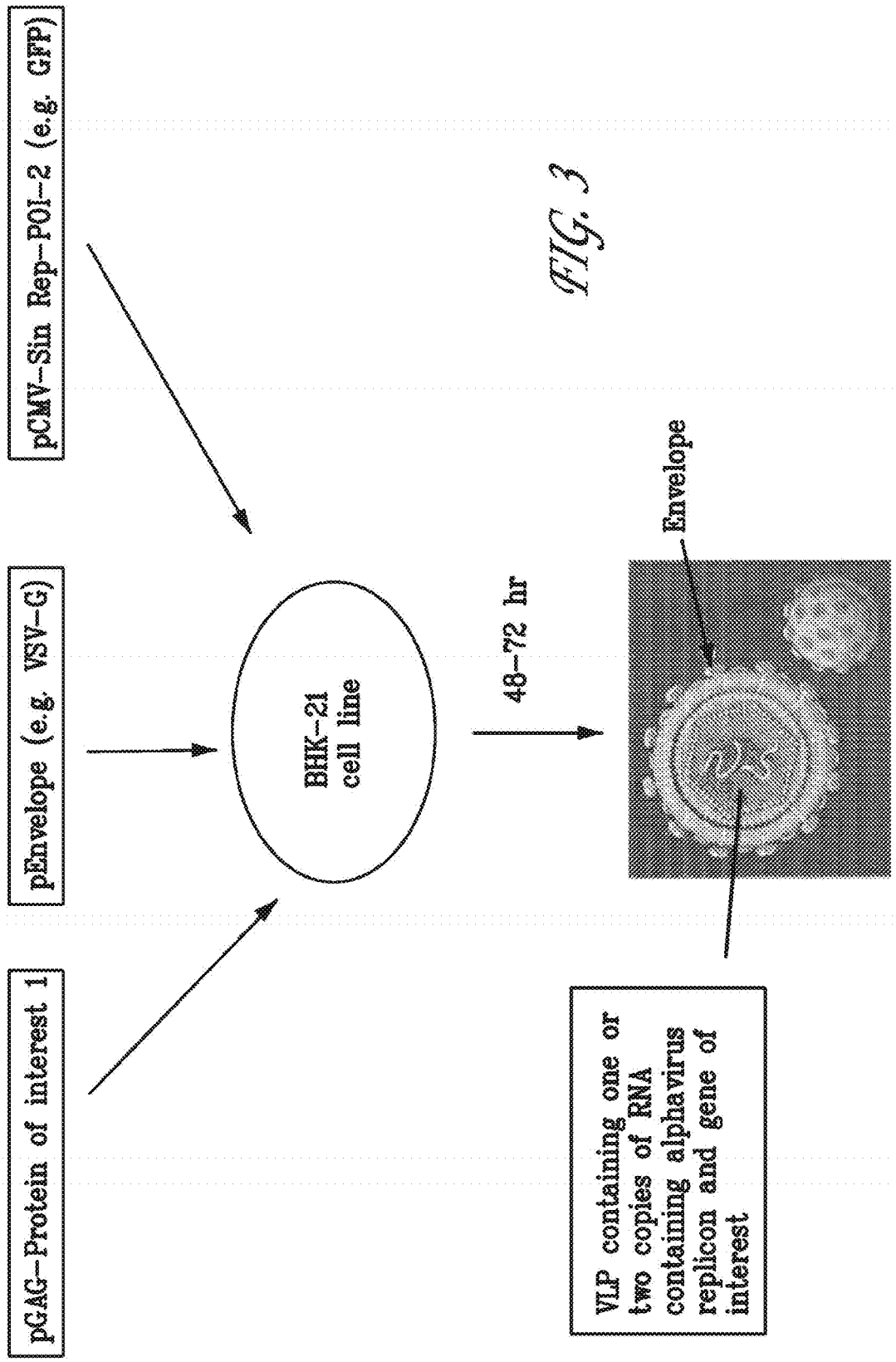

Once constructed the plasmids were tested for the ability to produce VLPs carrying a Sindbis virus replicon having a gene of interest. For these experiments, green fluorescent protein (GFP) was used as the gene of interest in order to facilitate detection of delivery and intracellular expression of the gene. To produce VLPs, each of the three plasmids described above were transfected into baby hamster kidney (BHK-21) cells using a standard nucleofection procedure with an Amaxa system according to manufacturer instructions (Lonza) (FIG. 3).

Briefly, the BHK-21 cells at 3×10$^6$ were re-suspended in 100 µl nucleofection solution L (Amaxa) and transferred to tube containing 4.5 µg of plasmid coding for GAG, 3 µg plasmid coding for VSV-G glycoprotein and 100 nanograms of plasmid coding for Sindbis alphavirus replicon or 2.5 micrograms for VEE replicon (in total volume of 10 µl). The mixture of cells and plasmids was transferred to nucleofection cuvette and nucleofected using Amaxa nucleofector II apparatus using settings for BHK-21. The nucleofected cells were re-suspended in 500 µl of completed culture medium and transferred to tissue culture plate containing culture medium solution and incubated at 37° C. for period of 72-96 hr or for 72 hr at 32° C. After this time supernatants consisting of VLPs and encapsidated alphavirus replicon was clarified by centrifugation at 3000 RPM/10 min at 4° C., filtered by 0.45 um filter and exposed to 10 units of DNAse I (Turbo™-DNAse (Ambion)) for 30 min at RT. Processed VLPs were stored at 4° C. or frozen on dry ice and transferred to −80° C. As a negative control (fusion-defective VLPs). BHK-21 cells were also nucleofected with only the pCMV-Sin Rep-POI-2 or VEEV-Rep-POI and pGAG-POI-1 plasmids, but not the pEnvelope plasmid encoding VSV-G. Following transfection, the cells were incubated for 48-72 hours in tissue culture medium under normal growth conditions to allow for plasmid-driven production of VLPs.

Figure 4A:
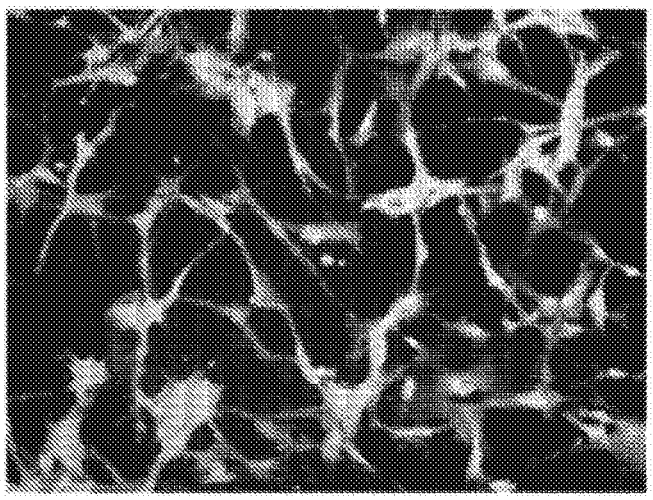
Figure 4B:
Figure 4C:
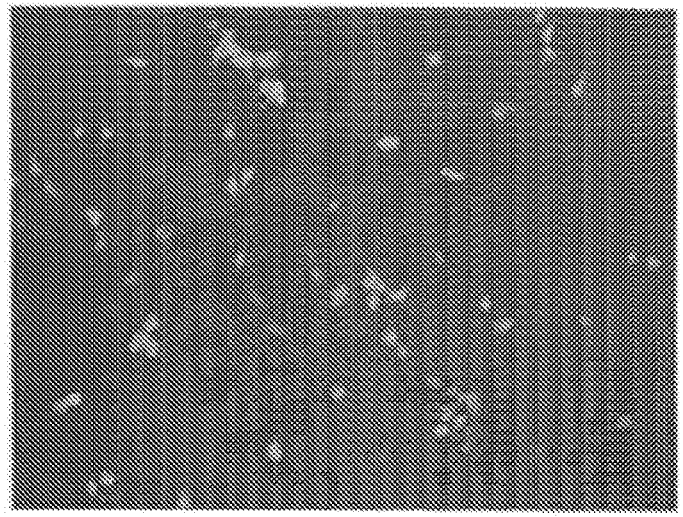

Once the transfected cells were finished incubating, the tissue culture supernatant, which should contain any produced VLPs, was collected. The collected cell supernatants were then added to cultured BHK-21 cells to determine if the cells could be successfully transduced with GFP. As shown in FIG. 4, cell supernatants collected from BHK-21 cells transfected with all three plasmids resulted in robust GFP expression when exposed to untransfected BHK-21 cells (FIG. 4A). Conversely, no GFP expression was observed for untransfected BHK-21 cells incubated with cell supernatants collected from BHK-21 cells transfected with only the pCMV-Sin Rep-POI-2 and pGAG-POI-1 plasmids (FIG. 4B). Similar experiments were also conducted using human embryonic kidney (HEK293T) cells to demonstrate that the constructed VLPs could transduce human cells (FIG. 4C). Furthermore, the constructed VLPs can also be stored at 4° C. for at least 30 days without losing the ability to transduce cells (FIG. 5A-5D).

Experiments were also conducted to assess the ability of VEEV-based alpha virus replicon to express protein in cells. For these studies BHK-21 cells were transduced with VLPs having a *Gaussia* luciferase gene inserted into a VEEV replicon. Following transduction, cell supernatants monitored for expression of luciferase protein. As shown in FIG. 6, high amounts of luciferase were detected in the supernatants of cells transduced with the VEEV replicon having the *Gaussia* luciferase gene (FIG. 6A, condition 4), relative to control VEEV replicons without an exogenous gene (condition 1), or with a gene encoding GFP (conditions 2 and 3). Additionally, expression of the luciferase protein increased rapidly after transduction (FIG. 6B). Similar results were also observed in the context of delivering functional cre recombinase (red cells) to cells engineered to express GFP in the absence of cre recombinase (FIG. 7B).

Cells were transduced in parallel with either Sindbis-based VLPs encoding GFP or VEEV-based VLPs encoding GFP. As shown in FIG. 8, both alphavirus-based VLPs caused robust GFP expression, while the cells transduced with VEEV-based VLPs were observed to have the higher expression levels (FIG. 8).

Example 2 miRNA Expressed by a VEE Alphavirus Replicon Inhibits Protein Production

Experiments were conducted to assess whether an alphavirus replicon encoding an miRNA sequence could inhibit protein production. To assess this, BHK-21 cells were transduced with a VLP replicon encoding GFP, miRNA specific for GFP, or cre recombinase (FIG. 9). (See the vectors shown in FIGS. 11 and 12, and SEQ ID NO: 1 in Table 1, below.) GFP expression was noticeable reduced when cells were first transduced with a replicon encoding miRNA for GFP and then subsequently transduced with a replicon encoding GFP (4 hours after the initial transduction), as compared to cells transduced with only a replicon encoding GFP (compare FIG. 9A with FIG. 9D). Conversely, when cells were first transduced with a replicon encoding cre recombinase and then subsequently transduced with a replicon encoding GFP (4 hours after the initial transduction), no significant reduction in GFP expression was apparent (FIG. 9G).

Example 3

Expression of Multiple Proteins in Target Cells Transduced with VEE VLPs

To assess whether an alphavirus replicon can express two separate proteins in the same cell, experiments were performed using a VEE replicon having HLA-DR1 under the control of one subgenomic promoter and CD80 under a another subgenomic promoter (FIG. 10A). Following production of VLPs having the described VEE replicon, cells were transduced and examined for expression of both proteins. As shown in FIG. 10B, transduced cells were able to express both proteins (immunolabeled HLA-DR1 is shown in green (FITC) and CD80 shown in red (phycoerythrin).

TABLE 1

SEQ ID NO: 1

1 gacggatcgg gagatctccc gatcccctat ggtgcactct cagtacaatc tgctctgatg 61 ccgcatagtt aagccagtat ctgctccctg cttgtgtgtt ggaggtcgct gagtagtgcg 121 cgagcaaaat ttaagctaca acaaggcaag gcttgaccga caattgcatg aagaatctgc 181 ttagggttag gcgttttgcg ctgcttcgcg atgtacgggc cagatatacg cgttgacatt 241 gattattgac tagttattaa tagtaatcaa ttacggggtc attagttcat agcccatata 301 tggagttccg cgttacataa cttacggtaa atggcccgcc tggctgaccg cccaacgacc 361 cccgcccatt gacgtcaata atgacgtatg ttcccatagt aacgccaata gggactttcc 421 attgacgtca atgggtggag tatttacggt aaactgccca cttggcagta catcaagtgt 481 atcatatgcc aagtacgccc cctattgacg tcaatgacgg taaatggccc gcctggcatt 541 atgcccagta catgacctta tgggactttc ctacttggca gtacatctac gtattagtca 601 tcgctattac catggtgatg cggttttggc agtacatcaa tgggcgtgga tagcggtttg 661 actcacgggg atttccaagt ctccacccca ttgacgtcaa tgggagtttg ttttggcacc 721 aaaatcaacg ggactttcca aaatgtcgta acaactccgc cccattgacg caaatgggcg 781 gtaggcgtgt acggtgggag gtctatataa gcagagctcg tatggacata ttgtcgttag TABLE 1-continued

```
 841 aacgcggcta caattaatac ataaccttat gtatcataca catacgattt aggggacact
 901 atagattgac ggcgtagtac acactattga atcaaacagc cgaccaattg cactaccatc
 961 acaatggaga agccagtagt aaacgtagac gtagaccccc agagtccgtt tgtcgtgcaa
1021 ctgcaaaaaa gcttcccgca atttgaggta gtagcacagc aggtcactcc aaatgaccat
1081 gctaatgcca gagcattttc gcatctggcc agtaaactaa tcgagctgga ggttcctacc
1141 acagcgacga tcttggacat aggcagcgca ccggctcgta gaatgttttc cgagcaccag
1201 tatcattgtg tctgccccat gcgtagtcca aagacccgg accgcatgat gaaatacgcc
1261 agtaaactgg cggaaaaagc gtgcaagatt acaaacaaga acttgcatga aagattaag
1321 gatctccgga ccgtacttga tacgccggat gctgaaacac catcgctctg ctttcacaac
1381 gatgttacct gcaacatgcg tgccgaatat tccgtcatgc aggacgtgta tatcaacgct
1441 cccggaacta tctatcatca ggctatgaaa ggcgtgcgga ccctgtactg gattggcttc
1501 gacaccaccc agttcatgtt ctcggctatg gcaggttcgt accctgcgta caacaccaac
1561 tgggccgacg agaaagtcct tgaagcgcgt aacatcggac tttgcagcac aaagctgagt
1621 gaaggtagga caggaaaatt gtcgataatg aggaagaagg agttgaagcc cgggtcgcgg
1681 gtttatttct ccgtaggatc gacactttat ccagaacaca gagccagctt gcagagctgg
1741 catcttccat cggtgttcca cttgaatgga aagcagtcgt acacttgccg ctgtgataca
1801 gtggtgagtt gcgaaggcta cgtagtgaag aaaatcacca tcagtcccgg gatcacggga
1861 gaaaccgtgg gatacgcggt tacacacaat agcgagggct tcttgctatg caaagttact
1921 gacacagtaa aaggagaacg ggtatcgttc cctgtgtgca cgtacatccc ggccaccata
1981 tgcgatcaga tgactggtat aatggccacg gatatatcac ctgacgatgc acaaaaactt
2041 ctggttgggc tcaaccagcg aattgtcatt aacggtagga ctaacaggaa caccaacacc
2101 atgcaaaatt accttctgcc gatcatagca caaggttca gcaaatgggc taaggagcgc
2161 aaggatgatc ttgataacga gaaaatgctg ggtactagag aacgcaagct tacgtatggc
2221 tgcttgtggg cgtttcgcac taagaaagta cattcgtttt atcgcccacc tggaacgcag
2281 acctgcgtaa aagtcccagc ctcttttagc gcttttccca tgtcgtccgt atggacgacc
2341 tctttgccca tgtcgctgag gcagaaattg aaactggcat tgcaaccaaa gaaggaggaa
2401 aaactgctgc aggtctcgga ggaattagtc atggaggcca aggctgcttt tgaggatgct
2461 caggaggaag ccagagcgga gaagctccga gaagcacttc caccattagt ggcagacaaa
2521 ggcatcgagg cagccgcaga agttgtctgc gaagtggagg ggctccaggc ggacatcgga
2581 gcagcattag ttgaaacccc gcgcggtcac gtaaggataa tacctcaagc aaatgaccgt
2641 atgatcggac agtatatcgt tgtctcgcca aactctgtgc tgaagaatgc caaactcgca
2701 ccagcgcacc cgctagcaga tcaggttaag atcataacac actccggaag atcaggaagg
2761 tacgcggtcg aaccatacga cgctaaagta ctgatgccaa caggaggtgc cgtaccatgg
2821 ccagaattcc tagcactgag tgagagcgcc acgttagtgt acaacgaaag agagtttgtg
2881 aaccgcaaac tataccacat tgccatgcat ggccccgcca agaatacaga gaggagcag
2941 tacaaggtta caaaggcaga gcttgcagaa acagagtacg tgtttgacgt ggacaagaag
3001 cgttgcgtta agaaggaaga agcctcaggt ctggtcctct cgggagaact gaccaaccct
3061 ccctatcatg agctagctct ggagggactg aagacccgac ctgcggtccc gtacaaggtc
3121 gaaacaatag gagtgatagg cacaccgggg tcgggcaagt cagctattat caagtcaact
3181 gtcacggcac gagatcttgt taccagcgga aagaaagaaa attgtcgcga aattgaggcc
```

TABLE 1-continued

```
3241 gacgtgctaa gactgagggg tatgcagatt acgtcgaaga cagtagattc ggttatgctc
3301 aacggatgcc acaaagccgt agaagtgctg tacgttgacg aagcgttcgc gtgccacgca
3361 ggagcactac ttgccttgat tgctatcgtc aggccccgca agaaggtagt actatgcgga
3421 gaccccatgc aatgcggatt cttcaacatg atgcaactaa aggtacattt caatcaccct
3481 gaaaaagaca tatgcaccaa gacattctac aagtatatct cccggcgttg cacacagcca
3541 gttacagcta ttgtatcgac actgcattac gatggaaaga tgaaaaccac gaacccgtgc
3601 aagaagaaca ttgaaatcga tattacaggg gccacaaagc cgaagccagg ggatatcatc
3661 ctgacatgtt tccgcgggtg ggttaagcaa ttgcaaatcg actatcccgg acatgaagta
3721 atgacagccg cggcctcaca agggctaacc agaaaaggag tgtatgccgt ccggcaaaaa
3781 gtcaatgaaa acccactgta cgcgatcaca tcagagcatg tgaacgtgtt gctcacccgc
3841 actgaggaca ggctagtgtg aaaaccttg cagggcgacc catggattaa gcagcccact
3901 aacataccta aggaaacttt tcaggctact atagaggact gggaagctga acacaaggga
3961 ataattgctg caataaacag ccccactccc cgtgccaatc cgttcagctg caagaccaac
4021 gtttgctggg cgaaagcatt ggaaccgata ctagccacgg ccggtatcgt acttaccggt
4081 tgccagtgga gcgaactgtt cccacagttt gcggatgaca aaccacattc ggccatttac
4141 gccttagacg taatttgcat taagtttttc ggcatggact tgacaagcgg actgttttct
4201 aaacagagca tcccactaac gtaccatccc gccgattcag cgaggccggt agctcattgg
4261 gacaacagcc aggaacccg caagtatggg tacgatcacg ccattgccgc cgaactctcc
4321 cgtagatttc cggtgttcca gctagctggg aagggcacac aacttgattt gcagacgggg
4381 agaaccagag ttatctctgc acagcataac ctggtcccgg tgaaccgcaa tcttcctcac
4441 gccttagtcc ccgagtacaa ggagaagcaa cccggcccgg tcaaaaaatt cttgaaccag
4501 ttcaaacacc actcagtact tgtggtatca gaggaaaaaa ttgaagctcc ccgtaagaga
4561 atcgaatgga tcgcccccgat tggcatagcc ggtgcagata agaactacaa cctggctttc
4621 gggtttccgc cgcaggcacg gtacgacctg gtgttcatca acattggaac taaatacaga
4681 aaccaccact ttcagcagtg cgaagaccat gcggcgacct taaaaaccct ttcgcgttcg
4741 gccctgaatt gccttaaccc aggaggcacc ctcgtggtga agtcctatgg ctacgccgac
4801 cgcaacagtg aggacgtagt caccgctctt gccagaaagt tgtcagggt gtctgcagcg
4861 agaccagatt gtgtctcaag caatacagaa atgtacctga ttttccgaca actagacaac
4921 agccgtacac ggcaattcac cccgcaccat ctgaattgcg tgatttcgtc cgtgtatgag
4981 ggtacaagag atggagttgg agccgcgccg tcataccgca ccaaaaggga gaatattgct
5041 gactgtcaag aggaagcagt tgtcaacgca gccaatccgc tgggtagacc aggcgaagga
5101 gtctgccgtg ccatctataa acgttggccg accagttta ccgattcagc cacggagaca
5161 ggcaccgcaa gaatgactgt gtgcctagga aagaaagtga tccacgcggt cggccctgat
5221 ttccggaagc acccagaagc agaagccttg aaattgctac aaaacgccta ccatgcagtg
5281 gcagacttag taaatgaaca taacatcaag tctgtcgcca ttccactgct atctacaggc
5341 atttacgcag ccggaaaaga ccgccttgaa gtatcactta actgcttgac aaccgcgcta
5401 gacagaactg acgcggacgt aaccatctat tgcctggata gaagtggaa ggaaagaatc
5461 gacgcggcac tccaacttaa ggagtctgta acagagctga aggatgaaga tatggagatc
5521 gacgatgagt tagtatggat tcatccagac agttgcttga gggaagaaa gggattcagt
5581 actacaaaag gaaaattgta ttcgtacttc gaaggcacca aattccatca agcagcaaaa
```

TABLE 1-continued

```
5641 gacatggcgg agataaaggt cctgttccct aatgaccagg aaagtaatga caactgtgt
5701 gcctacatat tgggtgagac catggaagca atccgcgaaa agtgcccggt cgaccataac
5761 ccgtcgtcta gcccgcccaa aacgttgccg tgcctttgca tgtatgccat gacgccagaa
5821 agggtccaca gacttagaag caataacgtc aaagaagtta cagtatgctc ctccacccc
5881 cttcctaagc acaaaattaa gaatgttcag aaggttcagt gcacgaaagt agtcctgttt
5941 aatccgcaca ctcccgcatt cgttcccgcc cgtaagtaca tagaagtgcc agaacagcct
6001 accgctcctc ctgcacaggc cgaggaggcc cccgaagttg tagcgacacc gtcaccatct
6061 acagctgata acacctcgct tgatgtcaca gacatctcac tggatatgga tgacagtagc
6121 gaaggctcac tttttcgag ctttagcgga tcggacaact ctattactag tatggacagt
6181 tggtcgtcag gacctagttc actagagata gtagaccgaa ggcaggtggt ggtggctgac
6241 gttcatgccg tccaagagcc tgcccctatt ccaccgccaa ggctaaagaa gatggcccgc
6301 ctggcagcgg caagaaaaga gcccactcca ccggcaagca atagctctga gtccctccac
6361 ctctcttttg gtggggtatc catgtccctc ggatcaattt tcgacggaga gacggcccgc
6421 caggcagcgg tacaaccccct ggcaacaggc cccacggatg tgcctatgtc tttcggatcg
6481 ttttccgacg gagagattga tgagctgagc cgcagagtaa ctgagtccga acccgtcctg
6541 tttggatcat ttgaaccggg cgaagtgaac tcaattatat cgtcccgatc agccgtatct
6601 tttccactac gcaagcagag acgtagacgc aggagcagga ggactgaata ctgactaacc
6661 ggggtaggtg gtacatatt ttcgacggac acaggccctg ggcacttgca aaagaagtcc
6721 gttctgcaga accagcttac agaaccgacc ttggagcgca atgtcctgga aagaattcat
6781 gccccggtgc tcgacacgtc gaaagaggaa caactcaaac tcaggtacca gatgatgccc
6841 accgaagcca acaaaagtag gtaccagtct cgtaaagtag aaaatcagaa agcctaaacc
6901 actgagcgac tactgtcagg actacgactg tataactctg ccacagatca gccagaatgc
6961 tataagatca cctatccgaa accattgtac tccagtagcg taccggcgaa ctactccgat
7021 ccacagttcg ctgtagctgt ctgtaacaac tatctgcatg agaactatcc gacagtagca
7081 tcttatcaga ttactgacga gtacgatgct tacttggata tggtagacgg gacagtcgcc
7141 tgcctggata ctgcaacctt ctgccccgct aagcttagaa gttacccgaa aaaacatgag
7201 tatagagccc cgaatatccg cagtgcggtt ccatcagcga tgcagaacac gctacaaaat
7261 gtgctcattg ccgcaactaa aagaaattgc aacgtcacgc agatgcgtga actgccaaca
7321 ctggactcag cgacattcaa tgtcgaatgc tttcgaaaat atgcatgtaa tgacgagtat
7381 tgggaggagt tcgctcggaa gccaattagg attaccactg agtttgtcac cgcatatgta
7441 gctagactga aaggccctaa ggccgccgca ctatttgcaa agacgtataa tttggtccca
7501 ttgcaagaag tgcctatgga tagattcgtc atggacatga aaagagacgt gaaagttaca
7561 ccaggcacga acacacaga agaaagaccg aaagtacaag tgatacaagc cgcagaaccc
7621 ctggcgactg cttacttatg cgggattcac cgggaattag tgcgtaggct tacggccgtc
7681 ttgcttccaa acattcacac gctttttgac atgtcggcgg aggattttga tgcaatcata
7741 gcagaacact tcaagcaagg cgacccggta ctggagacgg atatcgcatc attcgacaaa
7801 agccaagacg acgctatggc gttaaccggt ctgatgatct tggaggacct gggtgtggat
7861 caaccactac tcgacttgat cgagtgcgcc tttggagaaa tatcatccac ccatctacct
7921 acgggtactc gttttaaatt cggggcgatg atgaaatccg gaatgttcct cacactttt
7981 gtcaacacag ttttgaatgt cgttatcgcc agcagagtac tagaagagcg gcttaaaacg
```

TABLE 1-continued

```
 8041 tccagatgtg cagcgttcat tggcgacgac aacatcatac atggagtagt atctgacaaa
 8101 gaaatggctg agaggtgcgc cacctggctc aacatggagg ttaagatcat cgacgcagtc
 8161 atcggtgaga gaccaccta cttctgcggc ggatttatct tgcaagattc ggttacttcc
 8221 acagcgtgcc gcgtggcgga tccctgaaa aggctgttta agttgggtaa accgctccca
 8281 gccgacgacg agcaagacga agacagaaga cgcgctctgc tagatgaaac aaaggcgtgg
 8341 tttagagtag gtataacagg cactttagca gtggccgtga cgacccggta tgaggtagac
 8401 aatattacac ctgtcctact ggcattgaga acttttgccc agagcaaaag agcattccaa
 8461 gccatcagag gggaaataaa gcatctctac ggtggtccta aatagtcagc atagtacatt
 8521 tcatctgact aatactacaa caccaccacc tctagagctt gccgccacca tggtgagcaa
 8581 gggcgaggag ctgttcaccg gggtggtgcc catcctggtc gagctggacg gcgacgtgaa
 8641 cggccacaag ttcagcgtgt ccggcgaggg cgagggcgat gccacctacg gcaagctgac
 8701 cctgaagttc atctgcacca ccggcaagct gcccgtgccc tggcccaccc tcgtgaccac
 8761 cctgacctac ggcgtgcagt gcttcagccg ctaccccgac cacatgaagc agcacgactt
 8821 cttcaagtcc gccatgcccg aaggctacgt ccaggagcgc accatcttct tcaaggacga
 8881 cggcaactac aagacccgcg ccgaggtgaa gttcgagggc gacaccctgg tgaaccgcat
 8941 cgagctgaag ggcatcgact tcaaggagga cggcaacatc ctggggcaca gctggagta
 9001 caactacaac agccacaacg tctatatcat ggccgacaag cagaagaacg gcatcaaggt
 9061 gaacttcaag atccgccaca acatcgagga cggcagcgtg cagctcgccg accactacca
 9121 gcagaacacc cccatcggcg acggccccgt gctgctgccc gacaaccact acctgagcac
 9181 ccagtccgcc ctgagcaaag accccaacga gaagcgcgat cacatggtcc tgctggagtt
 9241 cgtgaccgcc gccgggatca ctcacggcat ggacgagctg tacaagtaaa gcggccgtga
 9301 gcatgcaggc cttgggccca atgatccgac cagcaaaact cgatgtactt ccgaggaact
 9361 gatgtgcata atgcatcagg ctggtacatt agatccccgc ttaccgcggg caatatagca
 9421 acactaaaaa ctcgatgtac ttccgaggaa gcgcagtgca taatgctgcg cagtgttgcc
 9481 acataaccac tatattaacc atttatctag cggacgccaa aaactcaatg tatttctgag
 9541 gaagcgtggt gcataatgcc acgcagcgtc tgcataactt ttattatttc ttttattaat
 9601 caacaaaatt tgtttttaa catttcaaaa aaaaaaaaa aaaaaaaaa aaaaaaaaa
 9661 aaagggaatt cctcgattaa ttaagcggcc gctcgagatg gcacacgtgt tacggtttta
 9721 ccgtcgacct ctagctagag cttggcgtaa tcatggtcat agctgtttcc tgtgtgaaat
 9781 tgttatccgc tcacaattcc acacaacata cgagccggaa gcataaagtg taaagcctgg
 9841 ggtgcctaat gagtgagcta actcacatta attgcgttgc gctcactgcc cgctttccag
 9901 tcgggaaacc tgtcgtgcca gctgcattaa tgaatcggcc aacgcgcggg gagaggcggt
 9961 ttgcgtattg ggcgctcttc cgcttcctcg ctcactgact cgctgcgctc ggtcgttcgg
10021 ctgcggcgag cggtatcagc tcactcaaag gcggtaatac ggttatccac agaatcaggg
10081 gataacgcag gaaagaacat gtgagcaaaa ggccagcaaa aggccaggaa ccgtaaaaag
10141 gccgcgttgc tggcgttttt ccataggctc cgcccccctg acgagcatca caaaaatcga
10201 cgctcaagtc agaggtggcg aaacccgaca ggactataaa gataccaggc gtttccccct
10261 ggaagctccc tcgtgcgctc tcctgttccg accctgccgc ttaccggata cctgtccgcc
10321 tttctccctt cgggaagcgt ggcgctttct catagctcac gctgtaggta tctcagttcg
10381 gtgtaggtcg ttcgctccaa gctgggctgt gtgcacgaac cccccgttca gcccgaccgc
```

TABLE 1-continued

```
10441 tgcgccttat ccggtaacta tcgtcttgag tccaacccgg taagacacga cttatcgcca
10501 ctggcagcag ccactggtaa caggattagc agagcgaggt atgtaggcgg tgctacagag
10561 ttcttgaagt ggtggcctaa ctacggctac actagaagaa cagtatttgg tatctgcgct
10621 ctgctgaagc cagttacctt cggaaaaaga gttggtagct cttgatccgg caaacaaacc
10681 accgctggta gcggtggttt ttttgtttgc aagcagcaga ttacgcgcag aaaaaaagga
10741 tctcaagaag atcctttgat cttttctacg gggtctgacg ctcagtggaa cgaaaactca
10801 cgttaaggga ttttggtcat gagattatca aaaggatct tcacctagat ccttttaaat
10861 taaaaatgaa gttttaaatc aatctaaagt atatatgagt aaacttggtc tgacagttac
10921 caatgcttaa tcagtgaggc acctatctca gcgatctgtc tatttcgttc atccatagtt
10981 gcctgactcc ccgtcgtgta gataactacg atacgggagg cttaccatc tggccccagt
11041 gctgcaatga taccgcgaga cccacgctca ccggctccag atttatcagc aataaaccag
11101 ccagccgaa gggccgagcg cagaagtggt cctgcaactt tatccgcctc catccagtct
11161 attaattgtt gccgggaagc tagagtaagt agttcgccag ttaatagttt gcgcaacgtt
11221 gttgccattg ctacaggcat cgtggtgtca cgctcgtcgt ttggtatggc ttcattcagc
11281 tccggttccc aacgatcaag gcgagttaca tgatccccca tgttgtgcaa aaaagcggtt
11341 agctccttcg gtcctccgat cgttgtcaga gtaagttgg ccgcagtgtt atcactcatg
11401 gttatggcag cactgcataa ttctcttact gtcatgccat ccgtaagatg cttttctgtg
11461 actggtgagt actcaaccaa gtcattctga aatagtgta tgcggcgacc gagttgctct
11521 tgcccggcgt caatacggga taataccgcg ccacatagca gaactttaaa agtgctcatc
11581 attggaaaac gttcttcggg gcgaaaactc tcaaggatct taccgctgtt gagatccagt
11641 tcgatgtaac ccactcgtgc acccaactga tcttcagcat cttttacttt caccagcgtt
11701 tctgggtgag caaaaacagg aaggcaaaat gccgcaaaaa agggaataag ggcgacacgg
11761 aaatgttgaa tactcatact cttccttttt caatattatt gaagcattta tcagggttat
11821 tgtctcatga gcggatacat atttgaatgt atttagaaaa ataaacaaat aggggttccg
11881 cgcacatttc cccgaaaagt gccacctgac gtc
//
```

What is claimed is:

1. A replication defective virus like particle (VLP) comprising:
   a. an alphavirus replicon isolated from a Sindbis virus or Venezuelan equine encephalitis (VEE) virus comprising a recombinant polynucleotide comprising: (i) a 5' sequence which initiates transcription of alphavirus RNA, (ii) a Rous sarcoma virus (RSV) packaging signal, (iii) a nucleotide sequence encoding Sindbis virus or Venezuelan equine encephalitis virus nonstructural proteins NSP1, NSP2 NSP3 and NSP4, (iv) one or more subgenomic mRNA promoter (sgp) for Sindbis or VEE-encoded RNA-dependent RNA polymerase, wherein said sgp is linked to a heterologous nucleic acid sequence, (v) a 3' untranslated region (URT) and (vi) a polyA tail, wherein said heterologous nucleic acid sequence replaces the alphavirus structural protein gene;
   b. a retroviral gag protein encoded by a polynucleotide comprising a genomic sequence of the RSV,
   c. a fusogenic envelope protein,
   wherein the VLP does not comprise or express a retroviral pol gene, and wherein the VLP is not cytopathic to a eukaryotic cell.

2. The VLP of claim 1, wherein the fusogenic envelope protein is encoded by a polynucleotide comprising a genomic sequence encoding an envelope protein selected from the group consisting of haemagglutinin, Rous sarcoma virus fusion protein, an E protein of tick borne encephalitis virus and dengue fever virus, the E1 protein of Semliki Forest virus, baculovirus envelope glycoprotein (gp64, Vesicular stomatitis (Indiana) virus-EnvA (VSV-EnvA), and Vesicular stomatitis (Indiana) virus-G (VSV-G) protein.

3. The VLP of claim 1, wherein the recombinant polynucleotide encodes an antisense RNA, that knocks down expression of a gene in the eukaryotic cell.

4. The VLP of claim 1, wherein the recombinant polynucleotide encodes a short hairpin RNA or small hairpin RNA (shRNA) or a microRNA (miRNA), wherein the shRNA or miRNA knocks down expression of a gene in the eukaryotic cell.

5. A method of producing the VLP of claim 1 comprising:
   a. co-transforming a eukaryotic cell with:
      i. a first vector comprising a polynucleotide sequence encoding the alphavirus replicon of claim 1.a;
      ii. a second vector comprising the polynucleotide of claim 1.b.; and
      iii. a third vector comprising a polynucleotide sequence encoding the fusogenic envelope protein of claim 1c.;
   b. culturing the co-transformed eukaryotic cell under conditions suitable to cause each vector to produce its encoded product, thereby producing the VLP; and
   c. isolating the VLP from the eukaryotic cell.

6. The VLP of claim 1, wherein the recombinant polynucleotide comprises a sequence that encodes for HLA-DR1 (MEW II) and CD80.

7. The VLP of claim 6, wherein the alphavirus replicon is from the VEE virus and the HLA-DR1 is under the control of one sgp and CD80 is under control of a different sgp.

* * * * *

SEQUENCE LISTING

<160> NUMBER OF SEQ ID NOS: 1

<210> SEQ ID NO 1
<211> LENGTH: 11913
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
```

-continued

```
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctcg tatggacata ttgtcgttag    840
aacgcggcta caattaatac ataaccttat gtatcataca catacgattt aggggacact    900
atagattgac ggcgtagtac acactattga atcaaacagc cgaccaattg cactaccatc    960
acaatggaga agccagtagt aaacgtagac gtagacccccc agagtccgtt tgtcgtgcaa   1020
ctgcaaaaaa gcttcccgca atttgaggta gtagcacagc aggtcactcc aaatgaccat   1080
gctaatgcca gagcattttc gcatctggcc agtaaactaa tcgagctgga ggttcctacc   1140
acagcgacga tcttggacat aggcagcgca ccggctcgta gaatgttttc cgagcaccag   1200
tatcattgtg tctgccccat gcgtagtcca gaagacccgg accgcatgat gaaatacgcc   1260
agtaaactgg cggaaaaagc gtgcaagatt acaaacaaga acttgcatga gaagattaag   1320
gatctccgga ccgtacttga tacgccggat gctgaaacac catcgctctg ctttcacaac   1380
gatgttacct gcaacatgcg tgccgaatat tccgtcatgc aggacgtgta tatcaacgct   1440
cccgaaacta tctatcatca ggctatgaaa ggcgtgcgga ccctgtactg gattggcttc   1500
gacaccaccc agttcatgtt ctcggctatg gcaggttcgt accctgcgta caacaccaac   1560
tgggccgaca gaaagtcct tgaagcgcgt aacatcggac tttgcagcac aaagctgagt   1620
gaaggtagga caggaaaatt gtcgataatg aggaagaagg agttgaagcc cgggtcgcgg   1680
gtttatttct ccgtaggatc gacactttat ccagaacaca gagccagctt gcagagctgg   1740
catcttccat cggtgttcca cttgaatgga aagcagtcgt acacttgccg ctgtgataca   1800
gtggtgagtt gcgaaggcta cgtagtgaag aaaatcacca tcagtcccgg gatcacggga   1860
gaaaccgtgg gatacgcggt tacacacaat agcgagggct tcttgctatg caaagttact   1920
gacacagtaa aaggagaacg ggtatcgttc cctgtgtgca cgtacatccc ggccaccata   1980
tgcgatcaga tgactggtat aatggccacg gatatatcac ctgacgatgc acaaaaactt   2040
ctggttgggc tcaaccagcg aattgtcatt aacggtagga ctaacaggaa caccaacacc   2100
atgcaaaatt accttctgcc gatcatagca caagggttca gcaaatgggc taaggagcgc   2160
aaggatgatc ttgataacga gaaaatgctg ggtactagag aacgcaagct tacgtatggc   2220
tgcttgtggg cgtttcgcac taagaaagta cattcgtttt atcgcccacc tggaacgcag   2280
acctgcgtaa aagtcccagc ctcttttagc gcttttccca tgtcgtccgt atggacgacc   2340
tctttgccca tgtcgctgag gcagaaattg aaactggcat tgcaaccaaa gaaggaggaa   2400
aaactgctgc aggtctcgga ggaattagtc atggaggcca aggctgcttt tgaggatgct   2460
caggaggaag ccagagcgga gaagctccga gaagcacttc caccattagt ggcagacaaa   2520
ggcatcgagg cagccgcaga agttgtctgc gaagtggagg ggctccaggc ggacatcgga   2580
gcagcattag ttgaaacccc gcgcggtcac gtaaggataa taccctcaagc aaatgaccgt   2640
```

```
atgatcggac agtatatcgt tgtctcgcca aactctgtgc tgaagaatgc caaactcgca    2700
ccagcgcacc cgctagcaga tcaggttaag atcataacac actccggaag atcaggaagg    2760
tacgcggtcg aaccatacga cgctaaagta ctgatgccag caggaggtgc cgtaccatgg    2820
ccagaattcc tagcactgag tgagagcgcc acgttagtgt acaacgaaag agagtttgtg    2880
aaccgcaaac tataccacat tgccatgcat ggccccgcca agaatacaga agaggagcag    2940
tacaaggtta caaaggcaga gcttgcagaa acagagtacg tgtttgacgt ggacaagaag    3000
cgttgcgtta agaaggaaga agcctcaggt ctggtcctct cgggagaact gaccaaccct    3060
ccctatcatg agctagctct ggagggactg aagacccgac ctgcggtccc gtacaaggtc    3120
gaaacaatag gagtgatagg cacaccgggg tcgggcaagt cagctattat caagtcaact    3180
gtcacggcac gagatcttgt taccagcgga aagaaagaaa attgtcgcga aattgaggcc    3240
gacgtgctaa gactgagggg tatgcagatt acgtcgaaga cagtagattc ggttatgctc    3300
aacggatgcc acaaagccgt agaagtgctg tacgttgacg aagcgttcgc gtgccacgca    3360
ggagcactac ttgccttgat tgctatcgtc aggccccgca agaaggtagt actatgcgga    3420
gaccccatgc aatgcggatt cttcaacatg atgcaactaa aggtacattt caatcaccct    3480
gaaaaagaca tatgcaccaa gacattctac aagtatatct cccggcgttg cacacagcca    3540
gttacagcta ttgtatcgac actgcattac gatggaaaga tgaaaaccac gaacccgtgc    3600
aagaagaaca ttgaaatcga tattacaggg gccacaaagc cgaagccagg ggatatcatc    3660
ctgacatgtt tccgcgggtg ggttaagcaa ttgcaaatcg actatcccgg acatgaagta    3720
atgacagccg cggcctcaca agggctaacc agaaaaggag tgtatgccgt ccggcaaaaa    3780
gtcaatgaaa acccactgta cgcgatcaca tcagagcatg tgaacgtgtt gctcacccgc    3840
actgaggaca ggctagtgtg gaaaaccttg caggcgacc catggattaa gcagcccact    3900 aacatacccta aggaaaactt tcaggctact atagaggact gggaagctga acacaaggga    3960
ataattgctg caataaacag ccccactccc cgtgccaatc cgttcagctg caagaccaac    4020
gtttgctggg cgaaagcatt ggaaccgata ctagccacgg ccggtatcgt acttaccggt    4080
tgccagtgga gcgaactgtt cccacagttt gcggatgaca aaccacattc ggccatttac    4140
gccttagacg taatttgcat taagtttttc ggcatggact tgacaagcgg actgttttct    4200
aaacagagca tcccactaac gtaccatccc ggcgattcag cgaggccggt agctcattgg    4260
gacaacagcc caggaacccg caagtatggg tacgatcacg ccattgccgc cgaactctcc    4320
cgtagatttc cggtgttcca gctagctggg aagggcacac aacttgattt gcagacgggg    4380
agaaccagag ttatctctgc acagcataac ctggtcccgg tgaaccgcaa tcttcctcac    4440
gccttagtcc ccgagtacaa ggagaagcaa cccggcccgg tcaaaaaatt cttgaaccag    4500
ttcaaacacc actcagtact tgtggtatca gaggaaaaaa ttgaagctcc ccgtaagaga    4560
atcgaatgga tcgccccgat tggcatagcc ggtgcagata agaactacaa cctggctttc    4620
gggtttccgc cgcaggcacg gtacgacctg gtgttcatca acattggaac taaatacaga    4680
aaccaccact ttcagcagtg cgaagaccat gcggcgacct aaaaaccct ttcgcgttcg    4740 gccctgaatt gccttaaccc aggaggcacc ctcgtggtga agtcctatgg ctacgccgac    4800
cgcaacagtg aggacgtagt caccgctctt gccagaaagt tgtcagggt gtctgcagcg    4860 agaccagatt gtgtctcaag caatacagaa atgtacctga ttttccgaca actagacaac    4920
agccgtacac ggcaattcac cccgcaccat ctgaattgcg tgatttcgtc cgtgtatgag    4980
```

```
ggtacaagag atggagttgg agccgcgccg tcataccgca ccaaaaggga gaatattgct    5040
gactgtcaag aggaagcagt tgtcaacgca gccaatccgc tgggtagacc aggcgaagga    5100
gtctgccgtg ccatctataa acgttggccg accagtttta ccgattcagc cacggagaca    5160
ggcaccgcaa gaatgactgt gtgcctagga aagaaagtga tccacgcggt cggccctgat    5220
ttccggaagc acccagaagc agaagccttg aaattgctac aaaacgccta ccatgcagtg    5280
gcagacttag taaatgaaca taacatcaag tctgtcgcca ttccactgct atctacaggc    5340
atttacgcag ccggaaaaga ccgccttgaa gtatcactta actgcttgac aaccgcgcta    5400
gacagaactg acgcggacgt aaccatctat tgcctggata gaagtggaa ggaaagaatc     5460
gacgcggcac tccaacttaa ggagtctgta acagagctga aggatgaaga tatggagatc    5520
gacgatgagt tagtatggat tcatccagac agttgcttga agggaagaaa gggattcagt    5580
actacaaaag gaaaattgta ttcgtacttc gaaggcacca aattccatca agcagcaaaa    5640
gacatggcgg agataaaggt cctgttccct aatgaccagg aaagtaatga acaactgtgt    5700
gcctacatat tgggtgagac catggaagca atccgcgaaa agtgcccggt cgaccataac    5760
ccgtcgtcta gcccgcccaa aacgttgccg tgcctttgca tgtatgccat gacgccagaa    5820
agggtccaca gacttagaag caataacgtc aaagaagtta cagtatgctc ctccaccccc    5880
cttcctaagc acaaaattaa gaatgttcag aaggttcagt gcacgaaagt agtcctgttt    5940
aatccgcaca ctcccgcatt cgttcccgcc cgtaagtaca tagaagtgcc agaacagcct    6000
accgctcctc ctgcacaggc cgaggaggcc cccgaagttg tagcgacacc gtcaccatct    6060
acagctgata acacctcgct tgatgtcaca gacatctcac tggatatgga tgacagtagc    6120
gaaggctcac tttttcgag ctttagcgga tcggacaact ctattactag tatggacagt    6180
tggtcgtcag gacctagttc actagagata gtagaccgaa ggcaggtggt ggtggctgac    6240
gttcatgccg tccaagagcc tgccctatt ccaccgccaa ggctaaagaa gatggcccgc     6300
ctggcagcgg caagaaaaga gcccactcca ccggcaagca atagctctga gtccctccac    6360
ctctcttttg gtggggtatc catgtccctc ggatcaattt tcgacggaga gacggcccgc    6420
caggcagcgg tacaacccct ggcaacaggc cccacggatg tgcctatgtc tttcggatcg    6480
ttttccgacg gagagattga tgagctgagc cgcagagtaa ctgagtccga acccgtcctg    6540
tttggatcat ttgaaccggg cgaagtgaac tcaattatat cgtcccgatc agccgtatct    6600
tttccactac gcaagcagag acgtagacgc aggagcagga ggactgaata ctgactaacc    6660
gggtaggtg gtacatatt ttcgacggac acaggccctg ggcacttgca aaagaagtcc      6720
gttctgcaga accagcttac agaaccgacc ttggagcgca atgtcctgga aagaattcat    6780
gccccggtgc tcgacacgtc gaaagaggaa caactcaaac tcaggtacca gatgatgccc    6840
accgaagcca acaaaagtag gtaccagtct cgtaaagtag aaaatcagaa agccataacc    6900
actgagcgac tactgtcagg actacgactg tataactctg ccacagatca gccagaatgc    6960
tataagatca cctatccgaa accattgtac tccagtagcg taccggcgaa ctactccgat    7020
ccacagttcg ctgtagctgt ctgtaacaac tatctgcatg agaactatcc gacagtagca    7080
tcttatcaga ttactgacga gtacgatgct tacttggata tggtagacgg gacagtcgcc    7140
tgcctggata ctgcaacctt ctgccccgct aagcttagaa gttacccgaa aaaacatgag    7200
tatagagccc cgaatatccg cagtgcggtt ccatcagcga tgcagaacac gctacaaaat    7260
gtgctcattg ccgcaactaa aagaaattgc aacgtcacgc agatgcgtga actgccaaca    7320
ctggactcag cgacattcaa tgtcgaatgc tttcgaaaat atgcatgtaa tgacgagtat    7380
```

```
tgggaggagt tcgctcggaa gccaattagg attaccactg agtttgtcac cgcatatgta    7440
gctagactga aaggccctaa ggccgccgca ctatttgcaa agacgtataa tttggtccca    7500
ttgcaagaag tgcctatgga tagattcgtc atggacatga aaagagacgt gaaagttaca    7560
ccaggcacga aacacacaga agaaagaccg aaagtacaag tgatacaagc cgcagaaccc    7620
ctggcgactg cttacttatg cgggattcac cgggaattag tgcgtaggct tacggccgtc    7680
ttgcttccaa acattcacac gcttttttgac atgtcggcgg aggattttga tgcaatcata    7740
gcagaacact tcaagcaagg cgacccggta ctggagacgg atatcgcatc attcgacaaa    7800
agccaagacg acgctatggc gttaaccggt ctgatgatct tggaggacct gggtgtggat    7860
caaccactac tcgacttgat cgagtgcgcc tttggagaaa tatcatccac ccatctacct    7920
acgggtactc gttttaaatt cggggcgatg atgaaatccg gaatgttcct cacacttttt    7980
gtcaacacag ttttgaatgt cgttatcgcc agcagagtac tagaagagcg gcttaaaacg    8040
tccagatgtg cagcgttcat tggcgacgac aacatcatac atggagtagt atctgacaaa    8100
gaaatggctg agaggtgcgc cacctggctc aacatggagg ttaagatcat cgacgcagtc    8160
atcggtgaga gaccaccttta cttctgcggc ggatttatct tgcaagattc ggttacttcc    8220
acagcgtgcc gcgtggcgga tcccctgaaa aggctgttta agttgggtaa accgctccca    8280
gccgacgacg agcaagacga agacagaaga gcgcgctctgc tagatgaaac aaaggcgtgg    8340
tttagagtag gtataacagg cactttagca gtggccgtga cgacccggta tgaggtagac    8400
aatattacac ctgtcctact ggcattgaga acttttgccc agagcaaaag agcattccaa    8460
gccatcagag gggaaataaa gcatctctac ggtggtccta aatagtcagc atagtacatt    8520
tcatctgact aatactacaa caccaccacc tctagagctt gccgccacca tggtgagcaa    8580
gggcgaggag ctgttcaccg gggtggtgcc catcctggtc gagctggacg gcgacgtgaa    8640
cggccacaag ttcagcgtgt ccggcgaggg cgagggcgat gccacctacg gcaagctgac    8700
cctgaagttc atctgcacca ccggcaagct gcccgtgccc tggcccaccc tcgtgaccac    8760
cctgacctac ggcgtgcagt gcttcagccg ctaccccgac cacatgaagc agcacgactt    8820
cttcaagtcc gccatgcccg aaggctacgt ccaggagcgc accatcttct tcaaggacga    8880
cggcaactac aagacccgcg ccgaggtgaa gttcgagggc gacaccctgg tgaaccgcat    8940
cgagctgaag ggcatcgact tcaaggagga cggcaacatc ctggggcaca agctggagta    9000
caactacaac agccacaacg tctatatcat ggccgacaag cagaagaacg gcatcaaggt    9060
gaacttcaag atccgccaca acatcgagga cggcagcgtg cagctcgccg accactacca    9120
gcagaacacc cccatcggcg acggccccgt gctgctgccc gacaaccact acctgagcac    9180
ccagtccgcc ctgagcaaag accccaacga gaagcgcgat cacatggtcc tgctggagtt    9240
cgtgaccgcc gccgggatca ctcacggcat ggacgagctg tacaagtaaa gcggccgtga    9300
gcatgcaggc cttgggccca atgatccgac cagcaaaact cgatgtactt ccgaggaact    9360
gatgtgcata atgcatcagg ctggtacatt agatccccgc ttaccgcggg caatatagca    9420
acactaaaaa ctcgatgtac ttccgaggaa gcgcagtgca taatgctgcg cagtgttgcc    9480
acataaccac tatattaacc atttatctag cggacgccaa aaactcaatg tatttctgag    9540
gaagcgtggt gcataatgcc acgcagcgtc tgcataactt ttattatttc ttttattaat    9600
caacaaaatt ttgttttttaa catttcaaaa aaaaaaaaaa aaaaaaaaaa aaaaaaaaaa    9660
aaagggaatt cctcgattaa ttaagcggcc gctcgagatg gcacacgtgt tacggtttta    9720
```

-continued

```
ccgtcgacct ctagctagag cttggcgtaa tcatggtcat agctgtttcc tgtgtgaaat    9780
tgttatccgc tcacaattcc acacaacata cgagccggaa gcataaagtg taaagcctgg    9840
ggtgcctaat gagtgagcta actcacatta attgcgttgc gctcactgcc cgctttccag    9900
tcgggaaacc tgtcgtgcca gctgcattaa tgaatcggcc aacgcgcggg gagaggcggt   9960
ttgcgtattg ggcgctcttc cgcttcctcg ctcactgact cgctgcgctc ggtcgttcgg   10020
ctgcggcgag cggtatcagc tcactcaaag gcggtaatac ggttatccac agaatcaggg   10080
gataacgcag gaaagaacat gtgagcaaaa ggccagcaaa aggccaggaa ccgtaaaaag   10140
gccgcgttgc tggcgttttt ccataggctc cgcccccctg acgagcatca caaaaatcga   10200
cgctcaagtc agaggtggcg aaacccgaca ggactataaa gataccaggc gtttccccct   10260
ggaagctccc tcgtgcgctc tcctgttccg accctgccgc ttaccggata cctgtccgcc   10320
tttctccctt cgggaagcgt ggcgctttct catagctcac gctgtaggta tctcagttcg   10380
gtgtaggtcg ttcgctccaa gctgggctgt gtgcacgaac cccccgttca gcccgaccgc   10440
tgcgccttat ccggtaacta tcgtcttgag tccaacccgg taagacacga cttatcgcca   10500
ctggcagcag ccactggtaa caggattagc agagcgaggt atgtaggcgg tgctacagag   10560
ttcttgaagt ggtggcctaa ctacggctac actagaagaa cagtatttgg tatctgcgct   10620
ctgctgaagc cagttacctt cggaaaaaga gttggtagct cttgatccgg caaacaaacc   10680
accgctggta gcggtggttt ttttgtttgc aagcagcaga ttacgcgcag aaaaaaagga   10740
tctcaagaag atcctttgat cttttctacg gggtctgacg ctcagtggaa cgaaaactca   10800
cgttaaggga ttttggtcat gagattatca aaaaggatct tcacctagat ccttttaaat   10860
taaaaatgaa gttttaaatc aatctaaagt atatatgagt aaacttggtc tgacagttac   10920
caatgcttaa tcagtgaggc acctatctca gcgatctgtc tatttcgttc atccatagtt   10980
gcctgactcc ccgtcgtgta gataactacg atacgggagg gcttaccatc tggccccagt   11040
gctgcaatga taccgcgaga cccacgctca ccggctccag atttatcagc aataaaccag   11100
ccagccggaa gggccgagcg cagaagtggt cctgcaactt tatccgcctc catccagtct   11160
attaattgtt gccgggaagc tagagtaagt agttcgccag ttaatagttt gcgcaacgtt   11220
gttgccattg ctacaggcat cgtggtgtca cgctcgtcgt ttggtatggc ttcattcagc   11280
tccggttccc aacgatcaag gcgagttaca tgatccccca tgttgtgcaa aaaagcggtt   11340
agctccttcg gtcctccgat cgttgtcaga agtaagttgg ccgcagtgtt atcactcatg   11400
gttatggcag cactgcataa ttctcttact gtcatgccat ccgtaagatg cttttctgtg   11460
actggtgagt actcaaccaa gtcattctga gaatagtgta tgcggcgacc gagttgctct   11520
tgcccggcgt caatacggga taataccgcg ccacatagca gaactttaaa agtgctcatc   11580
attggaaaac gttcttcggg gcgaaaactc tcaaggatct taccgctgtt gagatccagt   11640
tcgatgtaac ccactcgtgc acccaactga tcttcagcat cttttacttt caccagcgtt   11700
tctgggtgag caaaaacagg aaggcaaaat gccgcaaaaa agggaataag ggcgacacgg   11760
aaatgttgaa tactcatact cttcctttt caatattatt gaagcattta tcagggttat   11820
tgtctcatga gcggatacat atttgaatgt atttagaaaa ataaacaaat agggg ttccg   11880
cgcacatttc cccgaaaagt gccacctgac gtc                                11913
```